(12) United States Patent
Cohen et al.

(10) Patent No.: US 7,333,020 B2
(45) Date of Patent: Feb. 19, 2008

(54) DISPOSABLE ABSORBENT ARTICLE SYSTEM EMPLOYING SENSOR FOR DETECTING NON-NUTRITIVE SUCKING EVENTS

(75) Inventors: Jason C. Cohen, Appleton, WI (US); Peter D. Honer, Neenah, WI (US)

(73) Assignee: Kimberly - Clark Worldwide, Inc., Neenah, WI (US)

( * ) Notice: Subject to any disclaimer, the term of this patent is extended or adjusted under 35 U.S.C. 154(b) by 154 days.

(21) Appl. No.: 11/165,861

(22) Filed: Jun. 24, 2005

(65) Prior Publication Data
US 2006/0290517 A1 Dec. 28, 2006

(51) Int. Cl.
*G08B 17/00* (2006.01)
*A61F 13/15* (2006.01)
*A61J 17/00* (2006.01)

(52) U.S. Cl. ............... 340/573.1; 340/573.5; 340/586; 340/604; 604/358; 604/361; 604/362; 606/234; 606/235; 606/236

(58) Field of Classification Search ............ 340/573.1, 340/573.5, 586, 604; 606/234–236; 73/198; 604/358, 361, 362
See application file for complete search history.

(56) References Cited

U.S. PATENT DOCUMENTS

| | | | |
|---|---|---|---|
| 3,849,241 A | 11/1974 | Butin et al. |
| 4,663,220 A | 5/1987 | Wisneski et al. |
| 5,033,864 A | 7/1991 | Lasecki et al. |
| 5,147,343 A | 9/1992 | Kellenberger |
| 5,213,881 A | 5/1993 | Timmons et al. |
| 5,226,992 A | 7/1993 | Morman |
| 5,490,846 A | 2/1996 | Ellis et al. |
| 5,581,238 A | 12/1996 | Chang et al. |
| 5,601,542 A | 2/1997 | Melius et al. |
| 5,662,685 A | 9/1997 | Uhler |
| 5,695,868 A | 12/1997 | McCormack |

(Continued)

FOREIGN PATENT DOCUMENTS

EP 0 217 032 B1 2/1992

(Continued)

OTHER PUBLICATIONS

Gewolb, Ira H. et al., "Developmental Patterns of Rhythmic Suck and Swallow in Preterm Infants," *Developmental Medicine & Child Neurology*, vol. 43, 2001, pp. 22-27.

(Continued)

*Primary Examiner*—Benjamin C. Lee
*Assistant Examiner*—Lam Pham
(74) *Attorney, Agent, or Firm*—Denise L. Stoker; Sebastian C. Pugliese

(57) ABSTRACT

Disclosed is a system, method, and device for detecting non-nutritive sucking events produced by an infant; patterns comprising such events (i.e., rhythmic sucking patterns, or RSPs); and relating said events and/or RSPs to performance of a disposable absorbent article worn by the infant. The frequency and/or amplitude and/or other characteristics of non-nutritive sucking changes in response to liquid insults introduced to a disposable absorbent article. Accordingly, changes to RSPs offer detectable and measurable indicia of an infant's perception of the performance of a disposable absorbent article. Furthermore, such information may be used to support and/or substantiate marketing communications to consumers, or to guide selection and/or management of research-and-development programs.

23 Claims, 10 Drawing Sheets

U.S. PATENT DOCUMENTS

Figure 1:
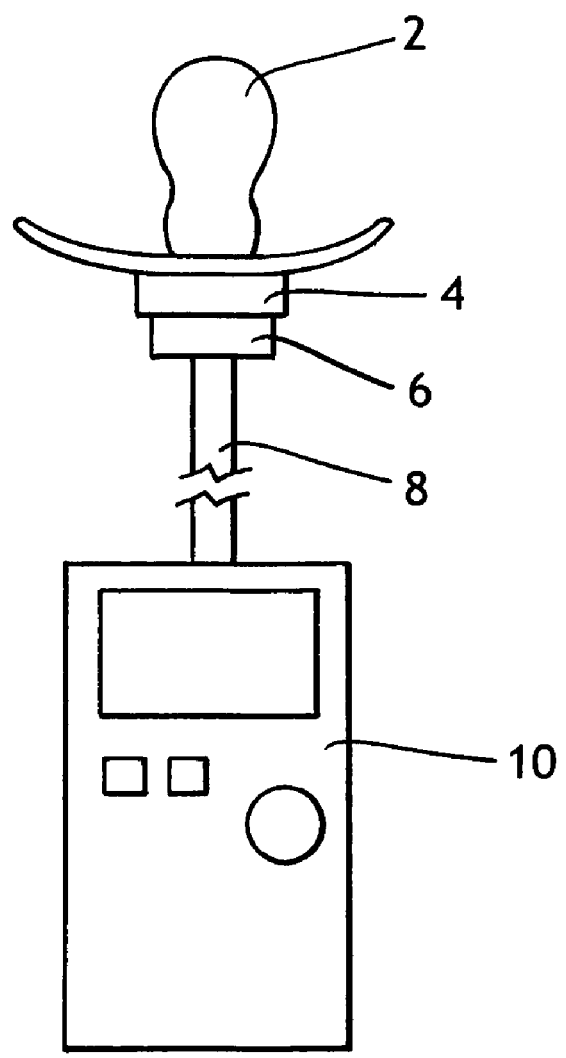

| | | | |
|---|---|---|---|
| 5,830,235 A * | 11/1998 | Standley | 606/234 |
| 5,843,056 A | 12/1998 | Good et al. | |
| 5,853,005 A | 12/1998 | Scanlon | |
| 5,859,585 A | 1/1999 | Fleming | |
| 5,903,222 A * | 5/1999 | Kawarizadeh et al. | 340/604 |
| 5,938,619 A | 8/1999 | Dogre Cuevas | |
| 6,033,367 A | 3/2000 | Goldfield | |
| 6,066,161 A * | 5/2000 | Parella | 606/234 |
| 6,102,935 A | 8/2000 | Harlan et al. | |
| 6,109,100 A * | 8/2000 | Buckley et al. | 73/198 |
| 6,149,934 A | 11/2000 | Krzysik et al. | |
| 6,238,379 B1 | 5/2001 | Keuhn, Jr. et al. | |
| 6,430,450 B1 | 8/2002 | Bach-y-Rita et al. | |
| 6,461,214 B1 * | 10/2002 | Lynch | 446/73 |
| 6,470,200 B2 | 10/2002 | Walker et al. | |
| 6,552,245 B1 | 4/2003 | Roessler et al. | |
| 6,591,140 B2 | 7/2003 | Strome et al. | |
| 6,686,843 B2 | 2/2004 | Felkowitz | |
| 6,870,479 B2 * | 3/2005 | Gabriel | 340/604 |
| 6,916,968 B2 * | 7/2005 | Shapira et al. | 604/361 |
| 6,966,904 B2 * | 11/2005 | Ruth et al. | 604/514 |
| 6,969,378 B1 | 11/2005 | Vukos et al. | |
| 2002/0052010 A1 | 5/2002 | Hisanaka et al. | |

FOREIGN PATENT DOCUMENTS

| | | |
|---|---|---|
| WO | WO 00/00151 A1 | 1/2000 |
| WO | WO 2003/048998 A2 | 6/2003 |

OTHER PUBLICATIONS

Kron, Reuben E. et al., "A Method of Measuring Sucking Behavior of Newborn Infants," *Psychosomatic Medicine: Journal of the American Psychosomatic Society*, vol. XXV, No. 2, 1963, pp. 181-191.

Akin, Frank J. et al., "A Refined Method to Evaluate Diapers for Effectiveness in Reducing Skin Hydration Using the Adult Forearm," *Skin Research and Technology*, 1997, pp. 173-176.

Hesketh, Sarah et al., "Non-nutritive Sucking and Sentence Processing," *Infant Behavior & Development*, vol. 20, No. 2, Apr.-Jun. 1997, pp. 263-269.

Nazzi, Thierry et al., "Language Discrimination by Newborns: Toward an Understanding of the Role of Rhythm," *Journal of Experimental Psychology: Human Perception and Performance*, vol. 24, No. 3, Jun. 1998, pp. 756-764.

Finan, Donald S. and Steven M. Barlow, "The Actifier: A Device for Neurophysiological Studies of Orofacial Control in Human Infants," *Journal of Speech & Hearing Research*, vol. 39, Issue 4, Aug. 1996, p. 833, 8 pages.

Barlow, Steven M. et al., "The University of Kansas Premie Neuroscience Research Program: Towards Universal Newborn Sensorimotor Screening and Habilitation," Merrill Advanced Studies Center, No. 104, Jun. 2000, viewed and printed from Internet web page "http://merrill.ku.edu/publications/2000whitepaper/barlow.html", 6 pages.

Barlow, Steven M. et al., "Mechanically Evoked Perioral Reflexes in Infants," Brain Research, vol. 599, No. 1, Dec. 18, 1992, pp. 158-160.

Segall, Zary, "Instrumented Pacifier," Slide No. 45 of "Beyond Wireless—Human Aware Technology and Design for Future Living," presentation available at Internet web page "http://www.hkstp.org/english/news/news_newsletter/Inno_Day_Prog_Rundown_PreDownload.files/Zary_presentation.pdf", 2005, 2 pages.

\* cited by examiner

DISPOSABLE ABSORBENT ARTICLE SYSTEM EMPLOYING SENSOR FOR DETECTING NON-NUTRITIVE SUCKING EVENTS

BACKGROUND

People rely on disposable absorbent articles, such as disposable diapers for infants, disposable training pants for toddlers, and incontinence products for adults, as part of their everyday lives.

Disposable absorbent articles are designed to absorb and contain body wastes. Caregivers use disposable absorbent articles for several reasons, including the convenience of the caregiver, and the health and comfort of the wearer of the disposable absorbent article. Accordingly, manufacturers of disposable absorbent articles spend considerable amounts of time and money on researching and developing: new disposable absorbent articles; new features for disposable absorbent articles; improved performance of existing disposable absorbent articles; and other related research-and-development activities. Manufacturers also spend significant sums of time and money communicating the existence and/or benefits of such new and/or improved disposable absorbent articles to consumers through advertising, packaging, and other marketing activities.

Unfortunately, the comfort, well-being, or stress level of an infant in relation to the performance of an existing, improved, or new disposable absorbent article may be difficult to determine and/or quantify. Generally, an infant provides signals as to his or her comfort, well being, or stress level in the form of facial expressions, other physical motions, and sounds. Some signals, such as smiling and cooing, may indicate that the infant is satisfied or happy with current environmental conditions and/or bodily conditions. Other signals, such as crying, generally indicate that the infant is not satisfied with current environmental conditions and/or bodily conditions. Such signals, whether indicative of a positive state of well being (smiling and cooing) or a negative state of well being (crying) may not be quantifiable and/or readily correlatable to the infant's perception of the disposable absorbent article, or its performance.

What is needed is a system, device, and method by which indicia of an infant's perception of a disposable absorbent article can be sensed, quantified, and used to help evaluate the performance of said article. The information obtained with such a system could be used for a variety of purposes, including: comparing the performance of a plurality of disposable-absorbent articles; changing the functional performance and/or technical specifications and/or materials-of-construction of a disposable-absorbent article in response to the obtained information; communicating messages to consumers regarding the performance of a disposable-absorbent article based on the obtained information; and other similar research-and-development and/or marketing activities.

SUMMARY

We have determined that non-nutritive sucking events produced by an infant, and patterns comprising such events (i.e., rhythmic sucking patterns), can be used to help evaluate the performance of a disposable absorbent article worn by the infant. A rhythmic sucking pattern comprises a pattern of individual, non-nutritive sucking events as evidenced by, for example, an infant sucking on a pacifier. We have confirmed that the frequency and/or amplitude and/or other characteristics of non-nutritive sucking changes in response to liquid insults introduced to a disposable absorbent article—in this case a disposable diaper—worn by an infant. Thus rhythmic sucking patterns, and changes to rhythmic sucking patterns, offer a detectable and measurable signal by which an infant's perception of a disposable absorbent article and/or its performance may be characterized.

One version of the invention is a system for evaluating a disposable article, the system comprising: a first sensor adapted to detect non-nutritive sucking events produced by an infant; a second sensor adapted to detect fluid flowing to, or present in, a disposable article worn by the infant; and an information device operatively connected to the first sensor, said information device adapted to accomplish one or more of receiving, storing, processing, displaying, or transmitting information corresponding to the non-nutritive sucking events detected by the first sensor.

In another version of the invention, the first sensor of the aforementioned system is a pressure transducer adapted to detect non-nutritive sucking events. The pressure transducer may be attached to a pacifier.

In some embodiments of the invention, the information device of the aforementioned system comprises a storage device, such as RAM (i.e., Random Access Memory), ROM (i.e., Read-Only Memory), EPROM (i.e., Erasable Programmable Read-Only Memory), PROM (i.e., Programmable Read-Only Memory), RFID (i.e., Radio Frequency IDentification), or the like. In some versions of the invention, the information device is attached to the pacifier referred to above.

In some versions of the invention, the information device of the aforementioned system is a computer.

In another embodiment, the second sensor of the aforementioned system is adapted to detect a property indicative of the flow of fluid to, or the presence of fluid in, a disposable absorbent article. Examples of such properties include temperature; humidity; current; mass flow rate; volumetric flow rate; mass; volume; opacity; transmittance; wavelength; the presence and/or concentration of dissolved solids, chemical compounds, ionic compounds, proteins, bacteria, microorganisms, suspended solids, precipitates, and the like; or some combination of these.

In some versions of the aforementioned system, the information device that is operatively connected to the first sensor is also operatively connected to the second sensor. Accordingly, said information device is further adapted to accomplish one or more of receiving, storing, processing, displaying, or transmitting information corresponding to the second sensor's detection of fluid flowing to, or presence in, the disposable article.

In other versions of the invention, the aforementioned system comprises a second information device that is operatively connected to the second sensor. The second information device is adapted to accomplish one or more of receiving, storing, processing, displaying, or transmitting information corresponding to the second sensor's detection of fluid flowing to, or presence in, the disposable article.

Another version of the invention is a pacifier adapted to detect non-nutritive sucking events, the pacifier comprising: a nipple; a base attached to said nipple; a sensor attached to said base, said sensor adapted to detect non-nutritive sucking events produced by an infant sucking on the nipple; and an information device attached to said base, wherein said device is operatively connected to the sensor, and wherein said information device is adapted to accomplish one or more of receiving, storing, processing, displaying, or transmitting information corresponding to the input detected by the sensor.

In one example of the invention, the sensor of the aforementioned pacifier is a pressure transducer adapted to detect non-nutritive sucking events.

In some embodiments of the invention, the information device of the aforementioned pacifier comprises a storage device, such as RAM (i.e., Random Access Memory), ROM (i.e., Read-Only Memory), EPROM (i.e., Erasable Programmable Read-Only Memory), PROM (i.e., Programmable Read-Only Memory), RFID (i.e., Radio Frequency IDentification), or the like.

Another version of the invention is a method for evaluating the performance of a disposable article, the method comprising the steps of: (a) detecting non-nutritive sucking events produced by an infant wearer of a disposable article; (b) detecting fluid flowing to, or present in, the disposable article worn by the infant; and (c) relating the detected non-nutritive sucking events to the detected flow of fluid to, or presence of fluid in, the disposable article.

In another version of the invention, the aforementioned method further comprises the steps of: repeating steps (a), (b), and (c)—listed in the previous paragraph—for a second disposable article (with the disposable article of the previous paragraph now being referred to as the first disposable article); and comparing the relationship obtained for the first disposable article to the relationship obtained for the second disposable article, or comparing the detected non-nutritive sucking events produced by an infant wearer of the first disposable article to the detected non-nutritive sucking events produced by an infant wearer of the second disposable article, or comparing the detected fluid flowing to, or present in, the first disposable article worn by the infant to the detected fluid flowing to, or present in, the second disposable article worn by the infant, or some combination of these.

In another example of the invention, one or both of the aforementioned methods further comprises communicating a message referring to a disposable absorbent article to consumers based on one or more of the aforementioned comparisons, relationships, or both.

Another version of the invention is a message referring to a disposable absorbent article and adapted to be communicated to consumers, wherein substantiation of the message is based, in whole or in part, on non-nutritive sucking events, rhythmic sucking patterns, or both. "Substantiation" refers to information that helps provide a reasonable basis for presenting some or all of the message.

Another embodiment of the invention is a research-and-development effort directed to changing the functional performance, product specifications, or materials of construction of a disposable article, wherein said research-and-development effort either incorporates, or is undertaken in response to, an evaluation of non-nutritive sucking events, rhythmic sucking patterns, or both.

These and other versions, embodiments, and examples of the invention are discussed elsewhere in this application.

DRAWINGS

FIG. 1 representatively illustrates a pacifier adapted to detect non-nutritive sucking events produced by a baby sucking on the pacifier.

Figure 2:
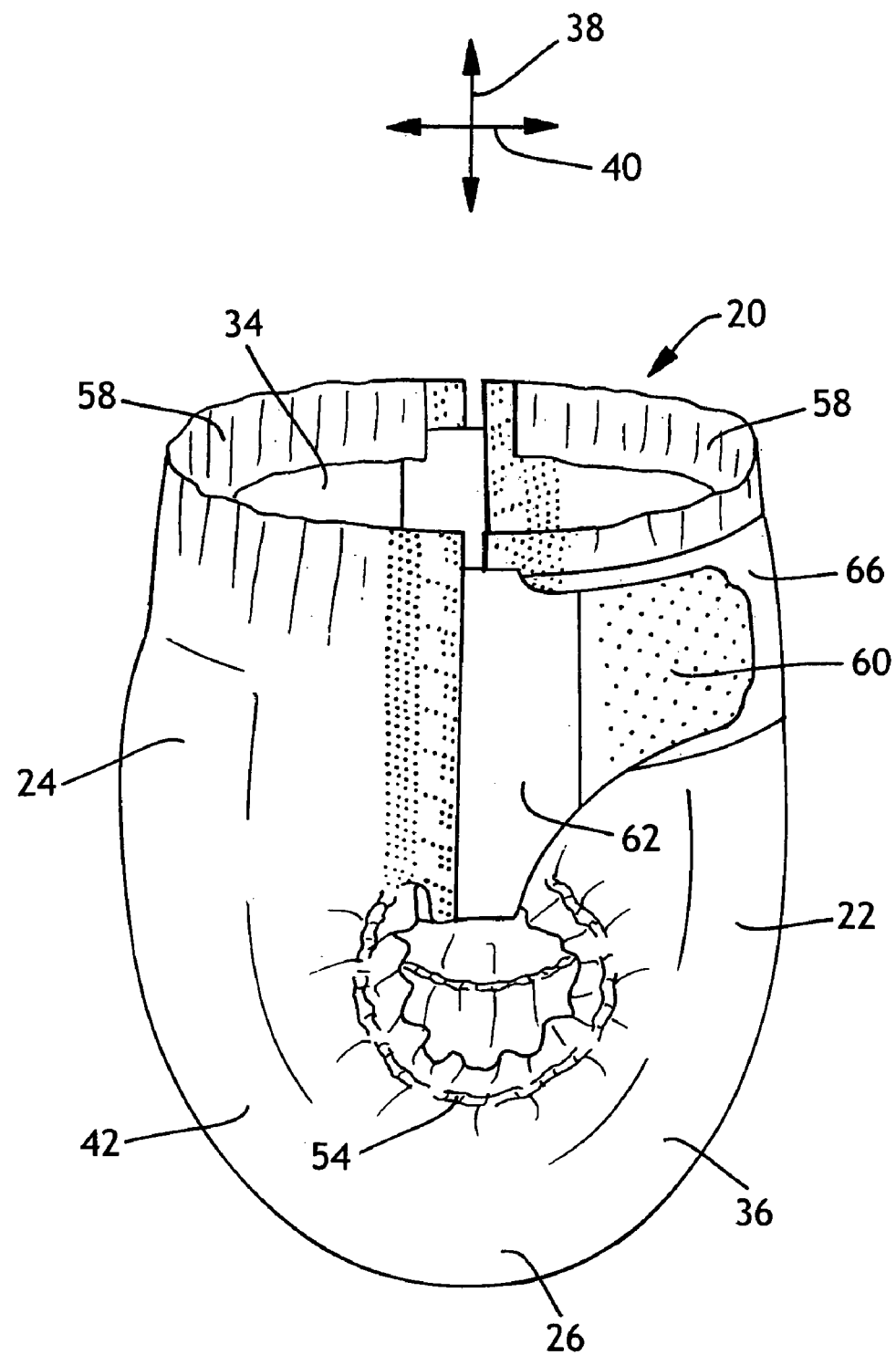

FIG. 2 representatively shows a perspective view of an example of a disposable absorbent article (an infant diaper).

Figure 3:
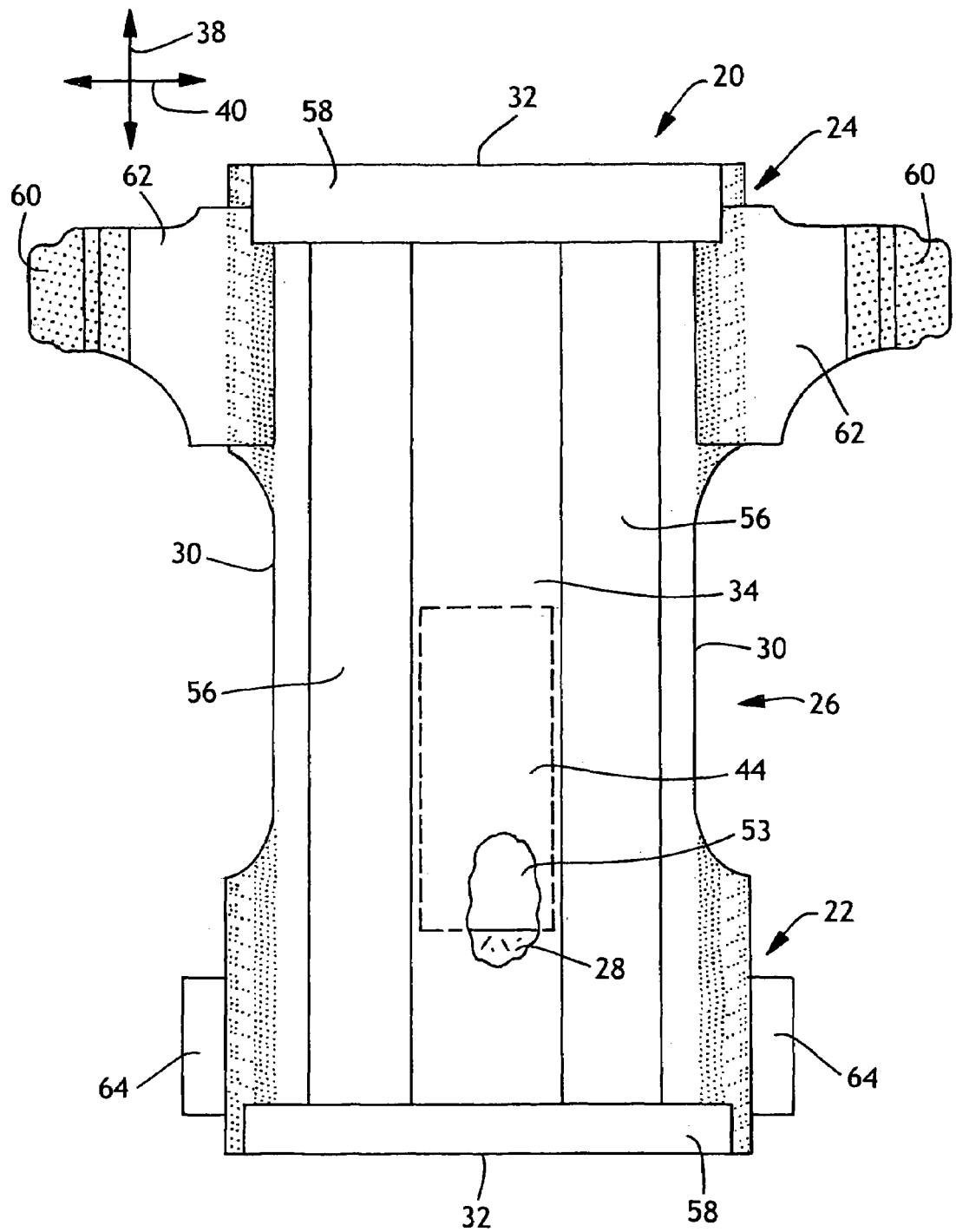
Figure 4:
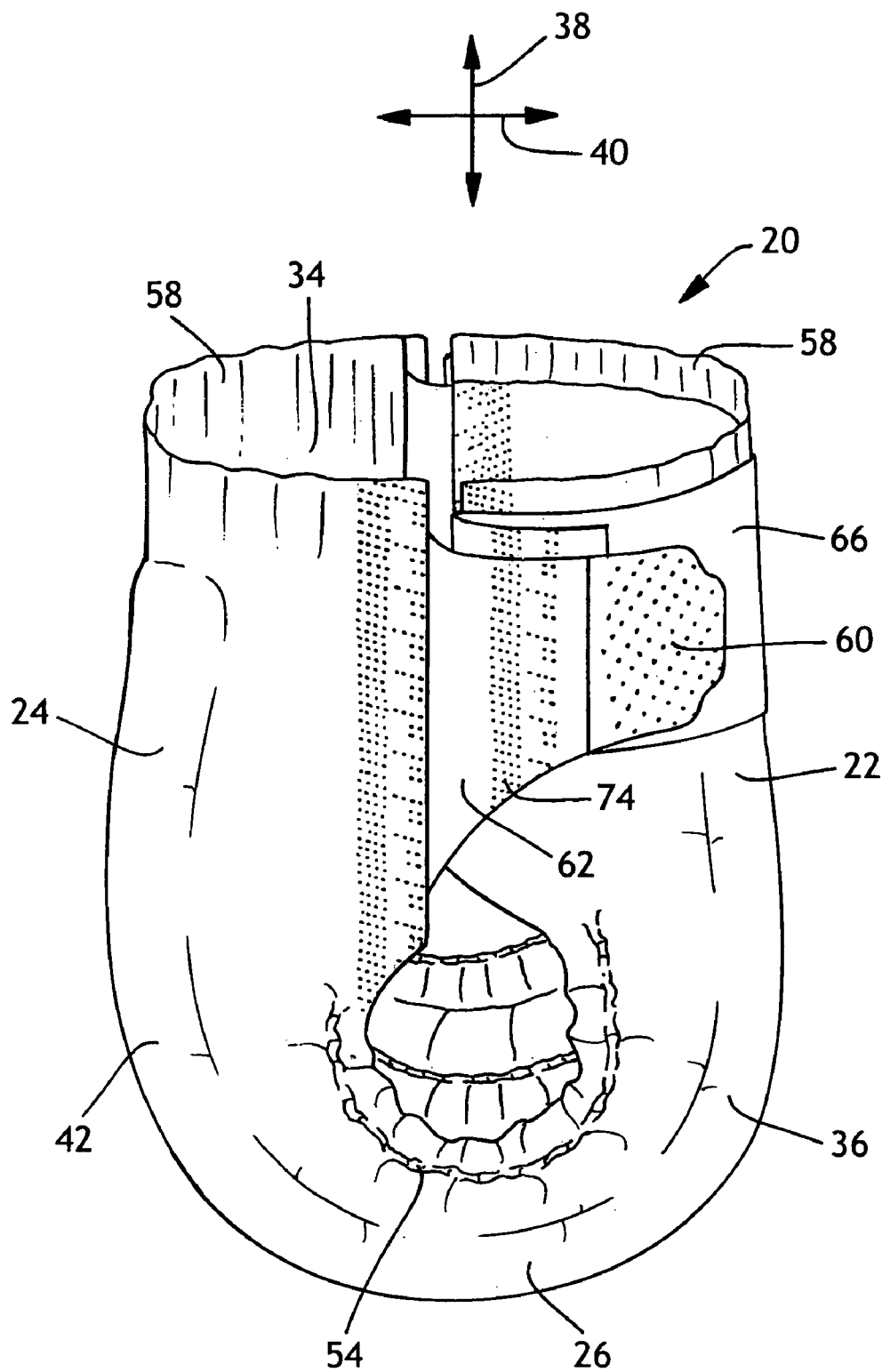

FIG. 3 representatively shows a plan view of the disposable absorbent article of FIG. 2 in an unfastened, stretched and laid flat condition with the surface of the article which contacts the wearer's skin facing the viewer and with portions of the article partially cut away to show the underlying features;

FIG. 4 representatively shows a perspective view of another example of a disposable absorbent article (a diaper pant).

Figure 5:
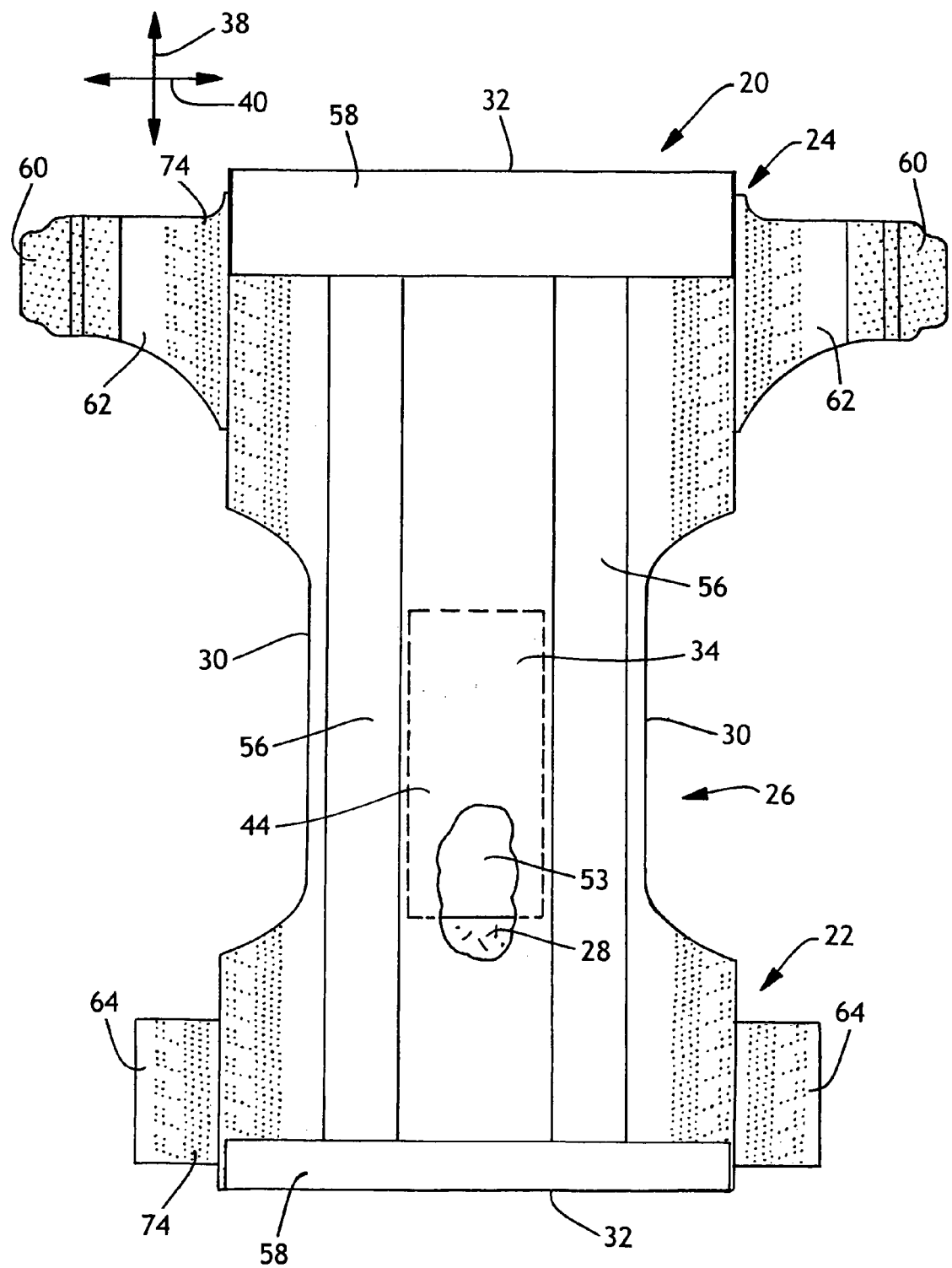

FIG. 5 representatively shows a plan view of the disposable absorbent article of FIG. 4 in an unfastened, stretched and laid flat condition with the surface of the article which contacts the wearer's skin facing the viewer and with portions of the article partially cut away to show the underlying features.

FIGS. 6A, 6B, 6C, 6D, 6E, and 6F representatively depict modification of a pacifier into one version of a device adapted to detect non-nutritive sucking events and/or rhythmic sucking patterns.

Figure 7:
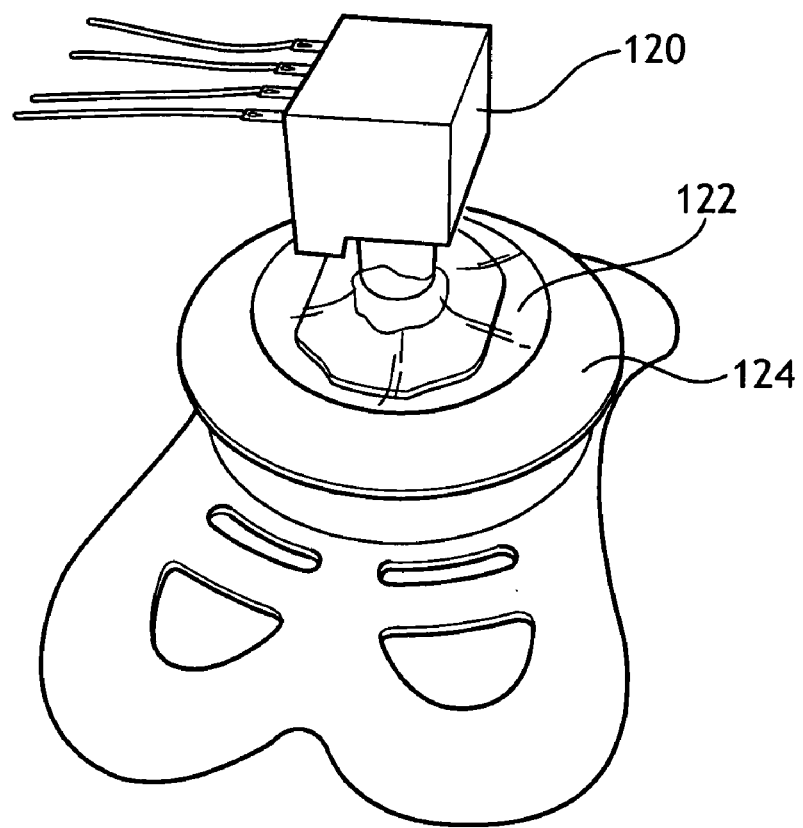

FIG. 7 representatively depicts modification of a pacifier into one version of a device adapted to detect non-nutritive sucking events and/or rhythmic sucking patterns.

Figure 8A:
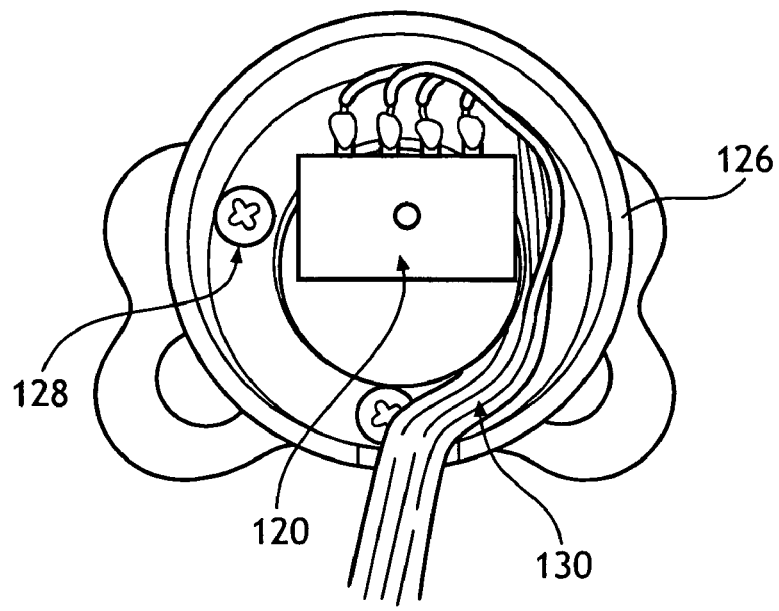
Figure 8B:
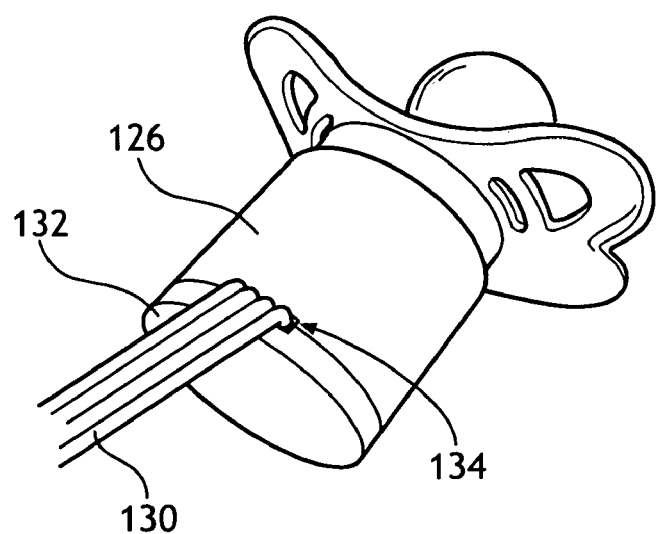

FIGS. 8A and 8B representatively depict modification of a pacifier into one version of a device adapted to detect non-nutritive sucking events and/or rhythmic sucking patterns.

Figure 9A:
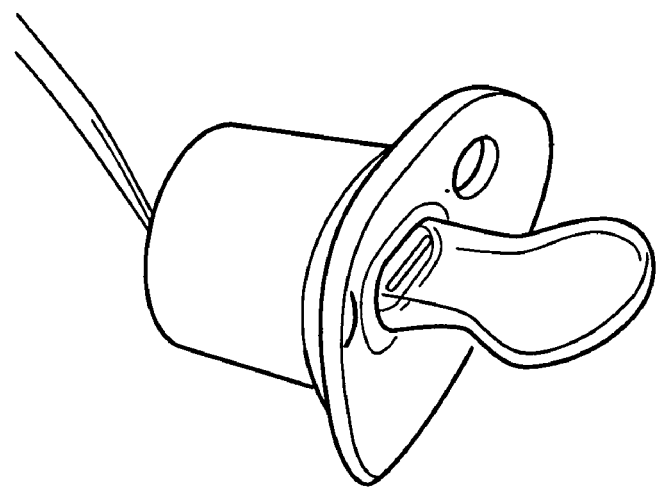
Figure 9B:
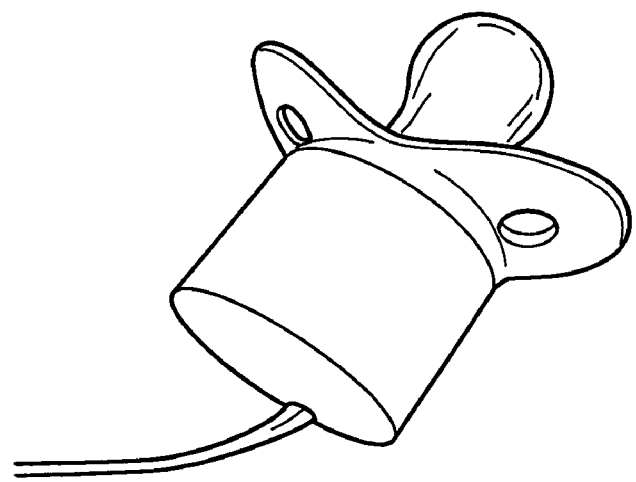

FIGS. 9A and 9B representatively depict another version of a device adapted to detect non-nutritive sucking events and/or rhythmic sucking patterns.

FIG. 10 representatively depicts a version of a system for detecting both non-nutritive sucking events/rhythmic sucking patterns and the flow of fluid to, or the presence of fluid in, a disposable absorbent article.

Corresponding reference characters indicate corresponding parts throughout the drawings.

DEFINITIONS

Within the context of this specification, each term or phrase below includes the following meaning or meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 25 percent (to 125 percent) of its relaxed length and will recover, upon release of the applied force, at least 40 percent of its elongation.

"Extensible" refers to a material or composite which is capable of extension or deformation without breaking, but does not substantially recover its original size and shape after removal of a force causing the extension or deformation. Suitably, an extensible material or composite can be elongated by at least 25 percent (to 125 percent) of its relaxed length.

"Fiber" refers to a continuous or discontinuous member having a high ratio of length to diameter or width. Thus, a fiber may be a filament, a thread, a strand, a yarn, or any other member or combination of these members.

"Fluid" refers to urine, a bowel movement ("BM"), a urine simulant, a BM simulant, or other such liquid or material.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons, et al. Meltblown fibers may be continuous or discontinuous and are generally self bonding when deposited onto a collecting surface.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Operatively connected" refers to the communication pathway by which one element, such as a sensor, communicates with another element, such as an information device. Communication may occur by way of an electrical connection through a conductive wire. Or communication may occur via a transmitted signal such as an infrared frequency, a radio frequency, or some other transmitted frequency signal. Alternatively, communication may occur by way of a mechanical connection, such as a hydraulic or pneumatic connection.

"Stretchable" means that a material can be stretched, without breaking, by at least 25 percent (to 125 percent of its initial (unstretched) length) in at least one direction. Elastic materials and extensible materials are each stretchable materials.

"Superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms may be defined with additional language in the remaining portions of the specification.

Description

Representative Devices and Sensors for Detecting Non-Nutritive Sucking Events

A representative device, adapted to detect non-nutritive sucking events produced by an infant, is depicted in FIG. 1, along with an information device. A nipple 2 is attached to a base 4. A sensor 6 is attached to the base so that an infant's sucking on the nipple is detected. For example, as outlined in the Examples section below, we modified commercially available pacifiers (e.g., a NUK®-brand pacifier made by NUK, MAPA GmbH, Industriestrasse 21-25, D—27404, Zeven, Germany; a MAM®-brand pacifier made by MAM Babyartikel GEsmbh, Lorenz-Mandl-Gasse 50, 1160 Wien, Austria; and a Disney®-brand/The-first-years®-brand pacifier made by The First Years, One Kiddie Drive, Avon, Mass.) by attaching a pressure transducer to the base of each pacifier using an epoxy glue. We used pressure transducers available from Omega Engineering, having offices at One Omega Drive, Box 4047, Stamford, Conn. As discussed below in the Examples section, three different pressure transducers, each capable of measuring different ranges of pressure, were used: (1) 0 to 1 pound per square inch (PSI) (model no. PX26-001GV, which corresponds to 0 to about 16.7 millivolts DC full scale); (2) 0 to 5 PSI (model no. PX26-005GV, which corresponds to 0 to about 50 millivolts DC full scale); and (3) 0 to 15 PSI (model no. PX26-015GV, which corresponds to 0 to about 100 millivolts DC full scale). An epoxy adhesive available from Cole-Parmer Instrument Company, having offices at 625 East Bunker Court, Vernon Hills, Ill., was used to attach the pressure transducer to the base of the pacifier. By operatively connecting the modified pacifier to a digital multimeter available from Fluke Corporation, having offices at 6920 Seaway Boulevard, Everett, Wash. (or, as described below, a computer having an analog-to-digital device), we were able to monitor changes in pressure inside the nipple of the modified pacifier. In FIG. 1, the operative connection is exemplified by a wire 8 connected to an information device 10, in this case the aforementioned multimeter. As mentioned elsewhere, the sensor 6 may be operatively connected to an information device in various ways, including use of a conductive wire, a selected portion of the electromagnetic spectrum (e.g., a wireless connection using radio waves), or a mechanical connection (e.g., a pneumatic connection).

An infant's sucking on the nipple causes the flexible nipple to stretch or extend, and then return to its original shape. This periodic extending or stretching of the nipple subjects the inside of the nipple to periodic compression, thereby changing the pressure inside the nipple. By operatively connecting a pressure transducer to the volume inside the nipple, the pressure inside the nipple, or a value corresponding to pressure inside the nipple, can be monitored. In some instances, we used a multimeter to display a reading, in millivolts, that corresponded to the pressure inside the nipple. In other cases we used a computer with an analog-to-digital device, and software adapted configure the computer for collecting and processing data, to process and display readings corresponding to the pressure inside the nipple. Additional detail regarding the construction of this modified pacifier, and its use, is given in the Examples section below.

Other sensors may be used to detect non-nutritive sucking events produced by an infant. For example, a strain gauge could be attached to a pacifier to detect any deflection or deformation of one or more elements of the pacifier (e.g., the nipple; the base to which the nipple is attached; etc.).

Alternatively, a sensor for detecting electrical signals associated with contraction of a muscle or muscle group could be used to detect non-nutritive sucking events produced by an infant. For example, a sensor comprising electrodes and capable of being adhered to skin could be used to detect such sucking events, whether effected by an infant sucking on a pacifier, the nipple on a bottle, the infant's own thumb, finger, or fingers, and the like.

If the non-nutritive sucking events produce sounds, then a device for monitoring audible events could be used to detect the sounds corresponding to non-nutritive sucking events.

While the preceding paragraphs provide examples of devices, sensors, and methods that may be used to detect non-nutritive sucking events produced by an infant, as well as different ways by which infants effect non-nutritive sucking events (e.g., by sucking on a pacifier, a nipple on a bottle, the infant's own thumb, etc.), other devices, sensors, methods, and ways of generating non-nutritive sucking events may be used, so long as the selected approach is capable of detecting the non-nutritive sucking events.

Representative Information Devices

A multimeter, discussed in the preceding paragraphs and in the Examples section below, is one version of an information device; i.e., a device adapted to accomplish one or more of receiving, storing, processing, displaying, or transmitting information, in this case information corresponding to non-nutritive sucking events produced by an infant, and detected by a sensor. For our work, the multimeter was used in some cases to display a reading, in millivolts, that corresponded to the pressure inside a modified pacifier. An infant's sucking on that pacifier produced a measurable rhythmic sucking pattern ("RSP")—i.e., a series of millivolt readings that we could plot and evaluate.

A variety of information devices may be used in conjunction with the present invention. For example, a computer may be used to monitor one or more values corresponding to the non-nutritive sucking events produced by an infant. Generally, a computer is capable of receiving, storing, processing, displaying, and transmitting information. Through the use of appropriate software, the computer can be configured to receive, store, process, display, and/or transmit information corresponding to non-nutritive sucking events produced by an infant. In our work, we used a computer to accumulate individual millivolt readings corresponding to individual non-nutritive sucking events. These readings were processed further to calculate an average value for an infant in an environment in which external stimuli remained relatively unchanged; and an average value in an environment in which external stimuli were changed in a controlled fashion (in this case, by activating a pump which transported a liquid to the diaper worn by the infant). This work is discussed in more detail below, but it is highlighted now to provide an example of how one version of an information device is used to quantify and process non-nutritive sucking events and rhythmic sucking patterns, which can provide indicia of an infant's perception of the performance of an absorbent article worn by the infant.

Many different information devices may be used with the present invention. In addition to a desktop computer or a device for recording and/or displaying readings corresponding to non-nutritive sucking events (e.g., a multimeter displaying millivolt readings), one could use a personal-digital assistant, hand-held computer, a portable computer, or other compact device to receive, store, process, display, and/or transmit information corresponding to non-nutritive sucking events produced by an infant. Alternatively, a chart recorder or other such device for recording the detected non-nutritive sucking events may be used. As noted above, the information device may comprise a storage device, including, for example, RAM (i.e., Random Access Memory), ROM (i.e., Read-Only Memory), EPROM (i.e., Erasable Programmable Read-Only Memory), PROM (i.e., Programmable Read-Only Memory), RFID (i.e., Radio Frequency IDentification), or the like. Furthermore, information devices comprising storage devices such as those identified in the preceding list may be compact enough to be attached to the sensor used to detect non-nutritive sucking events produced by an infant. For example, an RFID device could be incorporated into a pacifier such that the device recorded the non-nutritive sucking events produced by an infant sucking on the nipple of the pacifier. When desired, an external device could be used to read the stored information on the RFID element. Alternatively, the information on the RFID element could be viewed on a display, either on the pacifier itself, or on a computer or other information device remote from the pacifier. In some versions of the invention, the information device will comprise only a storage device.

In some versions of the invention, a display connected to the sensor itself (e.g. a pacifier having both a pressure transducer to sense the non-nutritive sucking events and an information device comprising a display) could provide an indication or information corresponding to non-nutritive sucking events detected by the sensor and/or stored on the information device. In some examples of the invention, the display could be graphical in nature, with displayed images corresponding to a psychological state or state of well being indicated by non-nutritive sucking events and/or rhythmic sucking patterns. So, for example, if certain rhythmic sucking patterns were generally determined to correspond to a more stressful condition for an infant, then the graphical display on the pacifier might, for example, be an image of a face with a frown. Alternatively, if certain rhythmic sucking patterns were generally determined to correspond to a less stressful condition for the infant, then the graphical display on the pacifier might, for example, be an image of a face with a smile. Furthermore, color might be used, either alone, or in conjunction with graphical images, to convey information regarding the well being, stress level, psychological state, or perceptions of the infant. Any hardware and software capable of presenting a display of information, graphical or otherwise, might be used, including, for example, liquid-crystal displays, light-emitting diodes, and the like. In some versions of the invention, the graphical display is associated with an information device remote from the sensor used to detect non-nutritive sucking events and/or rhythmic sucking patterns (as is discussed in more detail in the following paragraph).

It should be noted that the information device need only be operatively connected to the sensor used to detect non-nutritive sucking events. Accordingly, the information device might be attached to the sensor itself. Or the information device might be at a location remote from the sensor, with information conveyed by an appropriate wavelength in the electromagnetic spectrum (e.g., radio waves); a conductive wire; or some mechanical connection (e.g., a pneumatic or hydraulic connection). In some cases, the information device may comprise one or more components attached to the sensor used to detect non-nutritive sucking events, and one or more components at a location remote from the sensor.

Representative Approaches to Detecting the Presence of Fluid in a Disposable Absorbent Article As discussed above, the present invention is generally directed to systems, devices, and methods for detecting non-nutritive sucking events produced by an infant. An aspect of the present invention is to concurrently detect fluid flowing to, or present in, a disposable absorbent article worn by the infant. Some versions of the invention involve the transport of a liquid or simulant to a location on or in an absorbent article. In other versions of the invention, the presence of urine and/or BM in the disposable absorbent article is detected.

For example, in an experiment described in the Examples section below, we used a Masterflex peristaltic pump, available from Cole-Parmer Instrument Company, having offices at 625 East Bunker Court, Vernon Hills, Ill., to deliver a known volumetric flow rate of liquid, for a selected time interval, to a disposable absorbent article worn by an infant.

At the same time we were introducing liquid to the absorbent article, we continued to monitor the pattern of non-nutritive sucking events produced by the infant. As is discussed in the Examples section below, we determined that this pattern of non-nutritive sucking events—i.e., the rhythmic sucking pattern—changed after liquid was introduced to the disposable absorbent article worn by the infant.

Many other devices may be used to sense or detect the flow of fluid to, or present in, a disposable absorbent article. For example, as discussed in the preceding paragraph, a peristaltic pump may be used to transport liquid from a liquid source to the location at which the liquid is introduced to the disposable absorbent article. To determine the volumetric flow rate of the liquid, a user can correlate the rotational speed of the peristaltic pump head to the volumetric flow rate of the liquid being pumped. Alternatively, a user could connect a flow meter, such as a rotameter, to the tubing/piping used to convey liquid from the liquid source to the location at which the liquid is introduced to the absorbent article. Of course other types of pumps may be used, such as, for example, positive displacement pumps or centrifugal pumps. Alternatively, a reservoir could be positioned at a sufficient height above the location at which liquid is introduced to the absorbent article such that the force of gravity causes the liquid to flow. A pinch clamp, valve, or other device could be used to adjust said flow.

There are other ways of delivering the liquid or simulant to the absorbent article. For example, a volumetric pipette, beaker, flask, or other container or delivery device could be used to deliver liquid or simulant to the absorbent article. The volume, mass, or other property of the liquid or simulant being delivered to the absorbent article may be determined before, during, or after the liquid or simulant is delivered to the absorbent article.

A variety of different sensors may be used to detect the flow of liquid, including, for example, mass flow meters and/or volumetric flow meters. Other sensors may be used to detect the flow or presence of liquid. For example, one or more temperature sensors may be incorporated into a disposable article such that the presence of liquid, e.g., at a temperature corresponding to a typical body temperature (i.e., around 98 degrees Fahrenheit), would be detected by the sensor (assuming that ambient temperature, and the temperature of the absorbent article, were sufficiently different from the temperature of the liquid such that a change in temperature was detected when liquid was present). Other properties that could be sensed and indicative of the presence of liquid include, but are not limited to, humidity, current, mass, volume, opacity, transmittance, or wavelength. Furthermore, the presence of certain ingredients, compounds or organisms in a liquid could also be sensed or detected.

Note that many of these same approaches may be used to detect the presence of urine or BM in a disposable absorbent article. For example, sensors for detecting temperature, humidity, or both may be positioned in, or at a surface of, a disposable absorbent article in order to detect a urine or BM insult of an infant wearing the disposable absorbent article. Other sensors may be used, so long as the sensor is capable of detecting the presence of urine or BM in the disposable absorbent article.

One version of a system of the present invention will generally have a sensor for detecting non-nutritive sucking events and/or rhythmic sucking patterns; a sensor for detecting the flow of fluid to, or the presence of fluid in, a disposable absorbent article; and one or more information devices for receiving, storing, displaying, processing, and/or transmitting information corresponding to the detected non-nutritive sucking events and detected presence of flow of fluid.

Representative Disposable Article

The systems, devices, and methods of the present invention are used with disposable absorbent articles that are adapted to be worn by infants about the lower torso. As discussed above, the present invention may be used to help evaluate the performance of one or more absorbent articles. The present invention allows a manufacturer or other interested party to acquire data that provides an indication of an infant's perception of the performance of an absorbent article. It is understood that systems, devices, and methods of the present invention are equally adaptable for other types of absorbent articles.

FIG. 2 representatively illustrates an example of a refastenable disposable diaper, as generally indicated at 20, which can be evaluated using the present invention. FIG. 3 representatively illustrates the refastenable diaper of FIG. 2 in an unfastened, stretched and laid flat configuration with the surface of the diaper adapted to contact the wearer's skin facing the viewer and with portions of the diaper partially cut away to show the underlying features. FIG. 4 representatively illustrates another example of an absorbent article that can be evaluated using a system of the present invention, a diaper pant generally indicated at 20. FIG. 5 representatively illustrates the prefastened diaper pant of FIG. 4 in an unfastened, stretched and laid flat configuration with the surface of the diaper pant adapted to contact the wearer's skin facing the viewer and with portions of the diaper pant partially cut away to show the underlying features. As illustrated in FIG. 3 and FIG. 5, the diaper/diaper pant 20 defines a front waist region 22, a back waist region 24, a crotch region 26 that extends between and connects the front and back waist regions 22 and 24, a longitudinal direction 38 and a lateral direction 40. The front waist region 22 includes the portion of the diaper/diaper pant 20 that, when worn, is positioned on the front of the wearer while the back waist region 24 includes the portion of the diaper/diaper pant 20 that, when worn, is positioned on the back of the wearer. The crotch region 26 of the diaper/diaper pant 20 includes the portion of the diaper/diaper pant 20 that, when worn, is positioned between the legs of the wearer and covers the lower torso of the wearer.

The diaper/diaper pant 20 defines a pair of laterally opposed side edges 30, a pair of longitudinally opposed waist edges 32, an interior surface 34 that is configured to contact the wearer, and an exterior surface 36 opposite the interior surface 34 that is configured to contact the wearer's clothing in use. The illustrated diaper/diaper pant 20 also includes a substantially liquid impermeable outer cover 42 and a liquid permeable bodyside liner 44 that can be connected to the outer cover 42 in a superposed relation. An absorbent core 28 is located between the outer cover 42 and the bodyside liner 44. The laterally opposed side edges 30 of the diaper/diaper pant 20 are generally defined by the side edges of the outer cover 42 that further define leg openings that may be curvilinear. The waist edges 32 of the diaper/diaper pant 20 are generally defined by the waist edges of the outer cover 42 and define a waist opening that is configured to encircle the waist of the wearer when worn. The absorbent core 28 is configured to contain and/or absorb body exudates discharged from the wearer. The diaper/diaper pant 20 may further include leg elastics 54, containment flaps 56 and waist elastics 58 as are known to those skilled in the art. It should be recognized that individual components of the diaper/diaper pant 20 may be optional depending upon the intended use of the diaper/diaper pant 20.

The diaper/diaper pant 20 may further include refastenable mechanical fasteners 60. The mechanical fasteners 60 releasably engage the opposed side edges 30 of the diaper/diaper pant 20 in the opposite waist regions. The mechanical fasteners 60 can include a variety of materials and surfaces known for mechanical engagement such as buttons, pins, snaps, adhesive tape fasteners, cohesives, mushroom-and-loop fasteners and hook and loop fasteners. Further, the disposable diaper/diaper pant 20 may include an attachment panel 66 located on the front or back waist region 22 and 24, opposite the fasteners 60 to which the fasteners 60 can be releasably engaged during use of the diaper/diaper pant 20.

The diaper/diaper pant 20 may be of various suitable shapes. For example, in the unfastened configurations as illustrated in FIG. 3 and FIG. 5, the diaper/diaper pant 20 may have an overall rectangular shape, T-shape or an approximately hourglass shape. In the shown embodiments, the diaper/diaper pant 20 has a generally I-shape in an unfastened configuration.

The various components of the diaper/diaper pant 20 are integrally assembled together employing various types of suitable attachment means, such as adhesive, sonic and thermal bonds or combinations thereof. In the shown embodiments, for example, the outer cover 42 and bodyside liner 44 are assembled to each other and to the absorbent core 28 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent core 28 may be connected to the outer cover 42 using conventional fasteners such as buttons, hook and loop type fasteners, adhesive tape fasteners, and the like. The other components of the diaper/diaper pant 20 may be suitably connected together using similar means. Similarly, other diaper components, such as the elastic members 54 and 58 and the mechanical fasteners 60, may be assembled into the diaper/diaper pant 20 article by employing the above-identified attachment mechanisms. Desirably, the majority of the diaper components are assembled together using ultrasonic bonding techniques for reduced manufacturing cost.

The outer cover 42 of the diaper/diaper pant 20, as representatively illustrated in FIGS. 2 and 4, may suitably be composed of a material which is either liquid permeable or liquid impermeable. It is generally preferred that the outer cover 42 be formed from a material that is substantially impermeable to liquids. A typical outer cover 42 can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). The materials of the outer cover 42 can be thermally or adhesively laminated together. Suitable laminate adhesives, which can be applied continuously or intermittently as beads, a spray, parallel swirls, or the like, can be obtained from Bostik-Findley, Inc., of Wauwatosa, Wis., U.S.A., or from National Starch and Chemical Company, Bridgewater, N.J., U.S.A. If it is desired to present the outer cover 42 with a more cloth-like feeling, the outer cover 42 may be formed from a polyolefin film having a nonwoven web laminated to the exterior surface thereof, such as a spunbond web of polyolefin fibers. For example, a stretch-thinned polypropylene film having a thickness of about 0.015 millimeter (0.6 mil) may be thermally laminated thereto a spunbond web of polypropylene fibers. The polypropylene fibers may have a fiber diameter of about 15 to 20 microns, which nonwoven web has a basis weight of about 17 grams per square meter (0.5 ounce per square yard). The outer cover 42 may include bicomponent fibers such as polyethylene/polypropylene bicomponent fibers. Methods of forming such cloth-like outer covers are known to those skilled in the art. The outer cover 42 may also be an extensible outer cover such as the outer covers described in U.S. Pat. No. 6,552,245 issued on Apr. 22, 2003 to Roessler et al. The outer cover 42 may also be a biaxially stretchable outer cover such as the outer covers described in U.S. patent application Ser. No. 09/698,517 filed on Oct. 27, 2000 by Vukos et al.

The outer cover 42 may be formed of a woven or nonwoven fibrous web layer which has been totally or partially constructed or treated to impart a desired level of liquid impermeability to selected regions that are adjacent or proximate the absorbent core 28. Still further, the outer cover 42 may optionally be composed of a micro-porous "breathable" material which permits vapors to escape from the absorbent core 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued Dec. 9,1997 to McCormack et al. and U.S. Pat. No. 5,843,056 issued Dec. 1, 1998 to Good et al., the descriptions of which are hereby incorporated by reference. Still further, the outer cover 42 may also be an elastomeric material, such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13,1993 to Morman, and European Patent Application No. EP 0 217 032 published on Apr. 8, 1987 in the names of Taylor et al., the disclosures of which are hereby incorporated by reference. The outer cover 42 can also be embossed or otherwise provided with a matte finish to provide a more aesthetically pleasing appearance.

In order to reduce the perception that the outer cover 42 feels damp or clammy, the diapers/diaper pants 20 may include a spacer or ventilation layer (not shown in Figures) between the garment-facing surface of the absorbent core 28 and the outer cover 42. The ventilation layer may include one or more nonwoven materials, for example a spunbond-meltblown-spunbond nonwoven material.

The representative absorbent articles include a bodyside liner 44 in superimposed relation to the outer cover 42. The bodyside liner 44, as representatively illustrated in FIG. 3 and FIG. 5, suitably presents a bodyfacing surface that is compliant, soft feeling, and nonirritating to the wearer's skin. Further, the bodyside liner 44 may be less hydrophilic than the absorbent core 28, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent 28. The bodyside liner 44 can also be made from extensible materials as are described in U.S. Pat. No. 6,552,245 issued on Apr. 22, 2003 to Roessler et al. The bodyside liner 44 can also be made from biaxially stretchable materials as are described in U.S. patent application Ser. No. 09/698,517 filed on Oct. 27, 2000 by Vukos et al.

Various woven and nonwoven fabrics can be used for the bodyside liner 44. For example, the bodyside liner may be composed of a meltblown or spunbond web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In a particular embodiment, the bodyside liner 44 is made from a nonwoven, spunbond, polypropylene fabric composed of fibers having a fiber diameter of about 21 to 23 microns formed into a web having a basis weight of about 20 grams per square meter and a density of about 0.13 grams per cubic centimeter. The fabric may be surface treated with about 0.3 weight percent of a surfactant, such as a surfactant commercially available from Hodgson Textile Chemicals, Inc. under the trade designation AHCOVEL Base N-62. The surfactant may be applied by any conventional means, such as spraying, printing, brush coating or similar techniques. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto that is configured to be transferred to the wearer's skin. Suitable compositions for application to the bodyside liner 44 are described in U.S. Pat. No. 6,149,934 that issued to Krzysik et al. on Nov. 21, 2000.

The representative absorbent articles can include an absorbent core 28 disposed between the outer cover 42 and the bodyside liner 44. The absorbent core 28 of the diaper/diaper pant 20, as representatively illustrated in FIG. 2 and FIG. 4, may suitably include a matrix of hydrophilic fibers, such as a web of cellulosic fluff, mixed with particles of a high-absorbency material commonly known as superabsorbent material. In a particular aspect, the absorbent core 28 includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. Alternatively, the absorbent core 28 may include a laminate of fibrous webs and superabsorbent material or other suitable matrix for maintaining a superabsorbent material in a localized area.

The absorbent core 28 may have any of a number of shapes. For example, the absorbent core 28 may be rectangular, I-shaped, or T-shaped. It is generally preferred that the absorbent core 28 is narrower in the intermediate section than in the front or rear waist sections of the diaper 20. The absorbent core 28 may be provided by a single layer or, in the alternative, may be provided by multiple layers, all of which need not extend the entire length and width of the absorbent core 28. In a particular aspect, the absorbent core 28 can be generally T-shaped with the laterally extending cross-bar of the "T" generally corresponding to the front waist region 22 of the absorbent article for improved performance, especially for male infants.

The size and the absorbent capacity of absorbent core 28 should be compatible with the size of the intended wearer and the liquid loading imparted by the intended use of the absorbent article. Further, the size and the absorbent capacity of the absorbent core 28 can be varied to accommodate wearers ranging from infants through adults. In addition, it has been found that the densities and/or basis weights of the absorbent core 28 can be varied.

The high-absorbency material may be selected from natural, synthetic, and modified natural polymers and materials. The high-absorbency materials may be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent core 28 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. In general, the high absorbency material is present in the absorbent core 28 in an amount of from about 5 to about 90 percent by weight, desirably in an amount of at least about 30 percent by weight, and even more desirably in an amount of at least about 50 percent by weight based on a total weight of the absorbent core 28. For example, in a particular aspect, the absorbent core 28 may include a laminate which includes at least about 50 percent by weight and desirably at least about 70 percent by weight of high-absorbency material overwrapped by a fibrous web or other suitable material for maintaining the high-absorbency material in a localized area.

An example of high-absorbency material suitable for use is DRYTECH 2035 polymer available from Dow Chemical, a business having offices in Midland, Mich. Other suitable superabsorbents may include FAVOR SXM 880 polymer obtained from Stockhausen, a business having offices in Greensboro, N.C.

Optionally, a substantially hydrophilic tissue or nonwoven wrapsheet (not illustrated) may be employed to help maintain the integrity of the structure of the absorbent core 28. The wrapsheet is typically placed about the absorbent core 28 over at least the two major facing surfaces thereof. The wrapsheet may be composed of an absorbent cellulosic material, such as creped wadding or a high wet-strength tissue. In one aspect, the wrapsheet may be configured to provide a wicking layer that helps to rapidly distribute liquid over the mass of absorbent fibers constituting the absorbent core 28.

Due to the thinness of absorbent core 28 and the high absorbency material within the absorbent core 28, the liquid uptake rates of the absorbent core 28, by itself, may be too low, or may not be adequately sustained over multiple insults of liquid into the absorbent core 28. To improve the overall liquid uptake and air exchange, the diaper/diaper pant 20 may further include a porous, liquid-permeable layer of surge management material 53, as representatively illustrated in FIG. 3 and FIG. 5. The surge management layer 53 is typically less hydrophilic than the absorbent core 28, and has an operable level of density and basis weight to quickly collect and temporarily hold liquid surges, to transport the liquid from its initial entrance point and to substantially completely release the liquid to other parts of the absorbent core 28. This configuration can help prevent the liquid from pooling and collecting on the portion of the diaper/diaper pant 20 positioned against the wearer's skin, thereby reducing the feeling of wetness by the wearer. The structure of the surge management layer 53 also generally enhances the air exchange within the diaper/diaper pant 20.

Various woven and nonwoven fabrics can be used to construct the surge management layer 53. For example, the surge management layer 53 may be a layer composed of a meltblown or spunbond web of synthetic fibers, such as polyolefin fibers. The surge management layer 53 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 53 may be composed of a substantially hydrophobic material, and the hydrophobic material may optionally be treated with a surfactant or otherwise processed to impart a desired level of wettability and hydrophilicity. In a particular aspect, the surge management layer 53 includes a hydrophobic, nonwoven material having a basis weight of from about 30 to about 120 grams per square meter.

The absorbent articles can include additional components. For example, as representatively illustrated in FIGS. 2-5, the disposable diaper/diaper pant 20 may include a pair of containment flaps 56 that are configured to provide a barrier to the lateral flow of body exudates. The containment flaps 56 may be located along the laterally opposed side edges 30 of the diaper/diaper pant adjacent the side edges of the absorbent core 28. Each containment flap 56 typically defines an unattached edge that is configured to maintain an upright, perpendicular configuration in at least the crotch region 26 of the diaper/diaper pant 20 to form a seal against the wearer's body. The containment flaps 56 may extend longitudinally along the entire length of the absorbent core 28 or may only extend partially along the length of the absorbent core 28. When the containment flaps 56 are shorter in length than the absorbent core 28, the containment flaps 56 can be selectively positioned anywhere along the side edges 30 of diaper/diaper pant 20 in the crotch region 26. In a particular aspect, the containment flaps 56 extend along the entire length of the absorbent core 28 to better contain the body exudates. Such containment flaps 56 are generally well known to those skilled in the art.

The diaper/diaper pant 20 may further include elastics at the waist edges 32 and side edges 30 of the diaper/diaper pant 20 to further prevent leakage of body exudates and support the absorbent core 28. For example, as representatively illustrated in FIGS. 2-5, the diaper/diaper pant 20 may include a pair of leg elastic members 54 that are connected to the laterally opposed side edges 30 of the diaper/diaper pant 20 in the crotch region 26. The diaper/diaper pant 20 may also include a pair of waist elastic members 58 that is connected to the longitudinally opposed waist edges 32 of the diaper/diaper pant 20. The leg elastics 54 and waist elastics 58 are generally adapted to fit about the legs and waist of a wearer in use to maintain a positive, contacting relationship with the wearer to effectively reduce or eliminate the leakage of body exudates from the diaper/diaper pant 20.

Materials suitable for use as the leg elastics 54 and waist elastics 58 are well known to those skilled in the art. Exemplary of such materials are sheets or strands or ribbons of a polymeric, elastomeric material that may be adhered to the outer cover 42 in a stretched position, or that may be attached to the outer cover 42 while the outer cover is pleated, such that elastic constrictive forces are imparted to the outer cover 42. The leg elastics 54 may also include such materials as polyurethane, synthetic and natural rubber. The waist elastics 58 may be formed by elastic strands attached to the outer cover 42 or they may be formed by attaching separate pieces of stretchable materials to the waist regions of the article. For example, the waist elastics 58 may include a piece of stretch-bonded laminate material attached to the interior surface 34 of the article to form a waistband. Elasticity may be added or incorporated into the waist opening of absorbent articles utilizing a variety of known approaches.

The absorbent articles may include one or more components that extend laterally outward from the longitudinal sides of the article. Typically, the longitudinal sides are defined by the materials forming the chassis of the diaper/diaper pant 20. The chassis may be defined by the outer cover 42 and bodyside liner 44 materials. Components that extend laterally outward may include front ear portions 64 and back ear portions 62. The front ear portions 64 and the back ear portions 62 may be formed of one or more materials and may include laminates of materials. The front ear portions 64 and the back ear portions 62 improve the fit of the absorbent article. More specifically, the front ear portions 64 may provide additional coverage around the waist of the wearer and they may assist caregivers with positioning the front waist region 22 on the wearer of the article. The front ear portions 64 may also include mechanical fastening materials such that the front ear portions 64 contribute to the overall fastening system of the article. The back ear portions 62 may also provide coverage around the waist of the wearer. More specifically, the back ear portions 62 may provide the bridging material between the back waist region 24 of the article and the front waist region 22 such that the back ear portions 62 form part of the article's waist opening and an upper edge of the article's leg openings. Additionally, the back ear portions 62 may include fastening materials that facilitate joining of the back waist region 24 with the front waist region 22. For example, the back ear portions 62 may include fasteners 60 selected for engagement with an attachment panel 66 in the front waist region 22 of the article.

Presently available infant diapers typically include back ear portions 62 that include a stretchable material. When the back ear portions 62 include a stretchable material, the back ear portions 62 may increase the range with which the fasteners 60 may be engaged into the attachment panel 66 or directly into the outer cover 42. Further, when the back ear portions 62 include a stretchable material, the article may be worn by a greater range of users as a result of the increased fit range. An exemplary material from which the back ear portions 62 may be constructed is a necked bonded laminate material having two nonwoven (e.g. spunbond) facings with an elastomeric film (e.g. KRATON film) laminated in between. Other suitable stretchable materials are known in the art. Depending on the design of the article, it may also be desirable for the front ear portions 64 to include a stretchable material.

When the product form of the absorbent article is a training pant or a swim pant, the back ear portions 62 and the front ear portions 64 are understood to include the side panels that are attached to the longitudinal sides 30 of the article and also are attached to each other to form side seams of the article. Typically, the side panels of training pants and swim pants are made from stretchable materials. The side panels' ability to stretch allows these products to be pulled on the wearer like underpants.

The diaper pant 20 form (representatively illustrated in FIG. 4 and FIG. 5) may be described as a hybrid between an infant diaper that is typically removed and applied while the child is lying down and a training pant that is put on like underpants. The product form may be referred to as a diaper pant because the diaper pant may be applied and removed as either a diaper or a pant. A diaper pant may have a back ear portion 62 and a front ear portion 64 where the back ear portion 62 and front ear portion 64 are attached to each other by a passive side bond 74. The passive side bond 74 may be selected to be readily tearable by caregivers during the process of "converting" the diaper pant from a pant to a diaper. Desirably, the passive side bond 74 is easily opened/broken without tearing of the materials used to form the back ear portion 62 and the front ear portion 64.

With each of the product forms, the back ear portions 62 and the front ear portions 64 may be attached to the longitudinal side edges 30 of the article by bonding techniques, such as ultrasonic bonding. Use of ultrasonic bonding techniques tends to form discrete bond points. The bond patterns, as will be discussed herein, may be formed using known techniques such as adhesive, thermal, laser and pressure that are capable of forming the patterns. Ultrasonic bonding will be referred to for purposes of example. The back ear portions 62 and the front ear portions 64 may be attached to one or more of the chassis materials using one or more bond patterns. The articles may include an attachment area 76 where the attachment area 76 includes an overlapping area of the material forming the outer cover 42 and the material forming either a back ear portion 62 or a front ear portion 64. The attachment area 76 may further include a variegated bond pattern 70 and a uniform bond pattern 72 where each bond pattern provides attachment between the outer cover 42 material and the ear portion material. The attachment area 76 may also include an overlapping area of the material forming the bodyside liner 44 and the material forming either a back ear portion 62 or a front ear portion 64. Additionally, the attachment area 76 may include an overlapping area of the material forming the outer cover 42, the material forming the bodyside liner 44 and the material forming either a back ear portion 62 or a front ear portion 64.

The variegated bond pattern 70 may be formed by a plurality of bond points that are variable in location with respect to each other. Put differently, the bond points of the variegated bond pattern 70 may not all be located equidistantly from each other. While the bond points of the variegated bond pattern 70 may spaced irregularly with respect to each other, the variegated bond pattern 70 may have a repeating pattern appearance. The uniform bond pattern 72 may be formed by a plurality of bond points that are regular in location with respect to each other. Put differently, the bond points of the uniform bond pattern 72 are located generally equidistantly from each other. The variegated bond pattern 70 and the uniform bond pattern 72 may be immediately adjacent to each other as illustrated in FIG. 5 or the patterns may have some open space in between them. The bond patterns may be formed by ultrasonic bonds or by other bonding techniques capable of providing individual bond points.

Representative Uses of System of Present Invention

Information acquired using a system of the present invention may be used for a variety of purposes. By obtaining information pertaining to the well being, stress level, or other such indicator of an infant's perception of a disposable article and its performance, a person or company can elect to develop and transmit messages and/or communications to consumers based on said information. For example, a message could be developed pertaining to comparing indicia of an infant's perception of one disposable article and its performance to an infant's perception of a second disposable article and its performance. If the disposable articles differ relative to materials of construction (e.g., one or more of the basic components or sub-assemblies discussed above in the section entitled Representative Disposable Articles) and/or functional performance (e.g., absorbency; fit; etc.), and differences in characteristics of individual non-nutritive sucking events or rhythmic sucking patterns (e.g., average amplitude) provide indicia of an infant's perceiving of this difference, then a communication to consumers based on this information could be fashioned. The communication or message could take the form of a newspaper advertisement, a television advertisement, a radio or other audio advertisement, items mailed directly to addressees, items emailed to addresses, Internet Web pages or other such postings, free standing inserts, coupons, various promotions (e.g., trade promotions), co-promotions with other companies, copy and the like, boxes and packages containing the product (in this case a disposable absorbent article), and other such forms of disseminating information to consumers or potential consumers.

The above approach could also be used when evaluating an improvement to an existing product. For example, a communication or message could be developed pertaining to comparing indicia of an infant's perception of one disposable article and its performance to an infant's perception of an improved disposable article and its performance. If the existing and improved disposable articles differ relative to materials of construction (e.g., one or more of the basic components or sub-assemblies discussed above in the section entitled Representative Disposable Articles) and/or functional performance (e.g., absorbency; fit; etc.), and differences in characteristics of individual non-nutritive sucking events or rhythmic sucking patterns (e.g., average amplitude) provide indicia of an infant (or, more likely, populations of infants) perceiving this difference, then a communication to consumers based on this information could be fashioned and disseminated as discussed above.

A system of the present invention could also be used to formulate, modify, or terminate a research-and-development program based on the acquired information. If, for example, infants wearing a modified disposable article exhibited indicia of an improved state of well being, or lower stress level, compared to infants wearing an existing disposable article, then a company could elect to invest in a new research-and-development program in which the modification was further developed.

A system of the present invention could be used to evaluate changes to any of the components or elements of a disposable absorbent article described in the Representative Disposable Article section above, including, for example: changes to, or the addition of, fiber in an absorbent core; changes to, or the addition of, superabsorbent in an absorbent core; the attachment of superabsorbent to fiber (e.g., through the addition of a material that would bind the superabsorbent to fiber); an increase or decrease in the amount of superabsorbent in an absorbent core; the addition or removal of a layer in the disposable absorbent article; a change in the fit characteristics of the absorbent article (e.g., the nature, amount, or position of elastic, stretchable, or elastomeric materials in the disposable absorbent article; a change or modification to the bodyside liner; a change or modification to the outer cover; or some combination thereof. It should be understood that the present invention may be used to provide indicia of an infant's perception of the performance of a disposable absorbent article in relation to other changes, additions, or removals of elements of a disposable absorbent article.

Changes to any of these or other elements may be accompanied by changes to various measured properties, or qualitative feedback in use tests, typically used to characterize the performance of a disposable absorbent article, including, for example: absorbency under load; absorbent capacity; re-wet; propensity to leak; intake rate; skin wetness; TEWL (i.e., trans-epidermal water loss as measured using an evaporimeter; see, e.g. F. J. Akin, J. T. Lemmen, D. L. Bozarth, M. J. Garafalo, and G. L. Grove (1997) "A Refined Method to Evaluate Diapers for Effectiveness in Reducing Skin Hydration Using the Adult Forearm" Skin Research and Technology Vol. 3, 173-176, which is hereby incorporated by reference in its entirety in a manner consistent herewith) etc. Accordingly, a system of the present invention can be used to provide indicia of an infant's perception of changes to measured properties (i.e., properties detected or sensed by a sensor or measuring device) of a disposable absorbent article. Alternatively, a system of the present invention may be used to provide indicia of an infant's perception of a disposable absorbent article that is also characterized by qualitative feedback (e.g., information provided by a caregiver/participant in a use test regarding the qualitative performance of the tested disposable absorbent article.)

While persons of skill in the art of disposable absorbent articles are familiar with various tests by which the performance of disposable absorbent article may be characterized, including qualitative information obtained from participants in a use test, some examples of tests are presented in U.S. Pat. No. No. 5,147,343, entitled "Absorbent Products Containing Hydrogels with Ability to Swell Against Pressure," to Stanley R. Kellenberger; U.S. Pat. No. 5,601,542, entitled "Absorbent Composite," to Mark K. Melius et al.; U.S. Pat. No. 5,490,846, entitled "Surge Management Fibrous Nonwoven Web for Personal Care Absorbent Articles and the Like," to Clifford J. Ellis, et al.; U.S. Pat. No. 6,238,379 B1, entitled "Absorbent Article with Increased Wet Breathability," to Charles Paul Keuhn, Jr., et al; all of which are incorporated by reference in their entirety in a manner consistent herewith.

Of course the preceding paragraphs provide examples of measurements, tests, use tests, and other ways by which the performance of a disposable absorbent article may be characterized. It should be understood that the present invention may be used to provide indicia of an infant's perception of the performance of a disposable absorbent article in relation to other tests, characteristics, or measurements.

EXAMPLES

Example 1

Construction of One Version of a Device Adapted to Detect Non-Nutritive Sucking Events and/or Rhythmic Sucking Patterns

A Disney®-brand pacifier, manufactured by The First Years, One Kiddie Drive, Avon, Mass., was obtained.

Figure 6A:
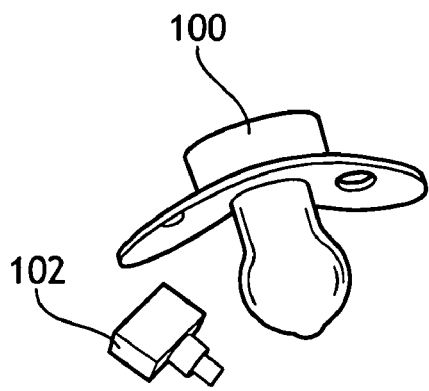
Figure 6B:
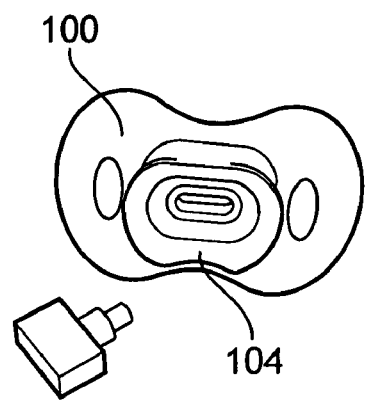

The pacifier was modified as depicted in FIGS. 6A through 6F. FIG. 6A depicts the pacifier 100 along with a pressure transducer 102 obtained from Omega Engineering, having offices at One Omega Drive, Box 4047, Stamford, Conn. This particular pressure transducer (model no. PX26-001 GV) was adapted to detect pressure readings from zero to one pounds per square inch. FIG. 6B depicts the pacifier 100 modified such that the back of the base has been removed to reveal the end of the nipple 104 which is attached to the base.

Figure 6C:
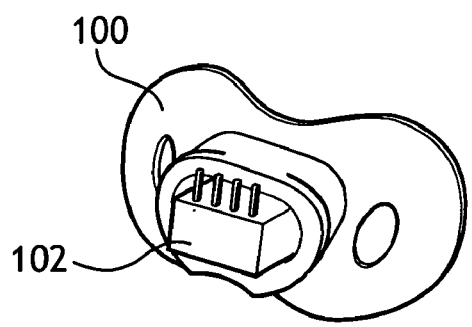
Figure 6D:
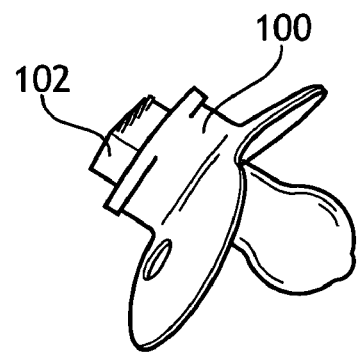

FIGS. 6C and 6D show the pressure transducer 102 inserted into the opening created by removing the back of the base. In this version of a device adapted to detect non-nutritive sucking events and/or rhythmic sucking patterns, epoxy is used to attach the pressure transducer 102 to the base of the pacifier. A sufficient amount of epoxy was used so that epoxy filled the space between the portion of the transducer that was inserted into the base and the inner wall of the base. i.e., a substantially air-tight seal was formed between the transducer and the base of the pacifier.

Figure 6E:
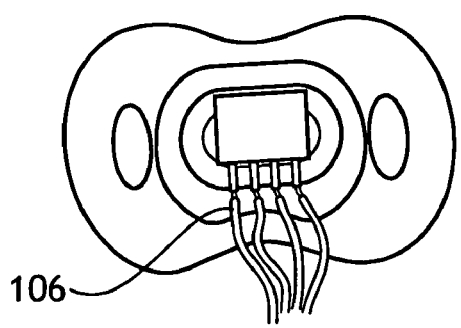
Figure 6F:
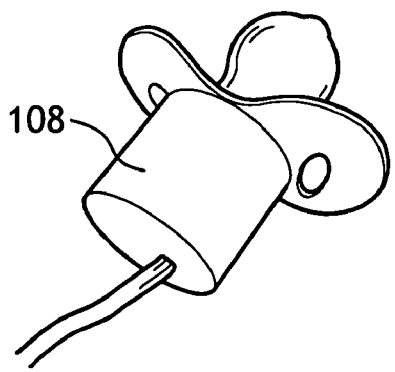

FIG. 6E shows a four-conductor ribbon cable 106 soldered to the pressure transducer. FIG. 6F depicts a protective sleeve 108 positioned around the pressure transducer.

Note also that a drill with a # 60 drill bit was used to drill a hole through the solidified epoxy (at a location near the transducer) such that a port to the open end of the nipple was created. The port allowed the nipple to vent air from its interior when squeezed or compressed; and to draw air into its interior when allowed to return to its original shape. The port allowed the nipple to collapse and return to its original shape during use. The port was added because the original, unmodified pacifier had a vent/port, but the original vent was eliminated when we removed the back of the pacifier and attached the transducer with epoxy.

Example 2

Construction of Another Version of a Device Adapted to Detect Non-Nutritive Sucking Events and/or Rhythmic Sucking Patterns

A MAM®-brand pacifier made by MAM Babyartikel GEsmbh, Lorenz-Mandl-Gasse 50, 1160 Wien, Austria, was obtained.

The pacifier was modified as follows. As depicted in FIG. 7, a pressure transducer 120, obtained from Omega Engineering, having offices at One Omega Drive, Box 4047, Stamford, Conn., was attached to the open end 122 of a base 124 of a pacifier. Epoxy was used to attach the pressure transducer to the pacifier. A sufficient amount of epoxy was used so that epoxy filled the space between the portion of the transducer that was inserted into the base and the inner wall of the base. I.e., a substantially air-tight seal was formed between the transducer and the base of the pacifier. This particular pressure transducer was adapted to detect pressure readings of zero to 5 pounds per square inch. As with Example 1, a #60 drill bit was used to drill a hole into the side of the epoxy such that a port to the open end of the nipple was created. The port allowed the nipple to vent air from its interior when squeezed or compressed; and to draw air into its interior when allowed to return to its original shape.

FIG. 8A depicts a protective cup 126 attached to the base of the pacifier using #2-56 screws 128. A four-conductor ribbon cable 130 was soldered to each of the four connectors of the pressure transducer. FIG. 8B shows the modified pacifier with an end cap 132 attached to the protective cup 126. A notch 134 allows for egress of the ribbon cable 130 from the interior of the protective cup 126.

Note also that a drill with a #60 drill bit was used to drill a hole through the solidified epoxy (at a location near the transducer) such that a port to the open end of the nipple was created. The port allowed the nipple to vent air from its interior when squeezed or compressed; and to draw air into its interior when allowed to return to its original shape. The port allowed the nipple to collapse and return to its original shape during use. The port was added because the original, unmodified pacifier had a vent/port, but the original vent was eliminated when we removed the back of the pacifier and attached the transducer with epoxy.

Example 3

Construction of Another Version of a Device Adapted to Detect Non-Nutritive Sucking Events and/or Rhythmic Sucking Patterns

A—Nuk®-brand pacifier, manufactured by NUK, MAPA GmbH, Industriestrasse 21-25, D-27404, Zeven, Germany, was obtained.

The pacifier was modified in the same way as the pacifier discussed in Example 2. In this case, however, a pressure transducer capable of detecting 0 to 15 pounds per square inch (0 to 100 millivolt DC, output) was attached to the base of the pacifier. The pressure transducer (model no. PX26-015GV; 0-15 psi) was obtained from Omega Engineering, having offices at One Omega Drive, Box 4047, Stamford, Conn.

FIGS. 9A and 9B depict two different views of this version of a device adapted to detect non-nutritive sucking events and/or rhythmic sucking patterns.

Example 4

One Version of a System for Evaluating a Disposable Absorbent Article

Figure 10A:
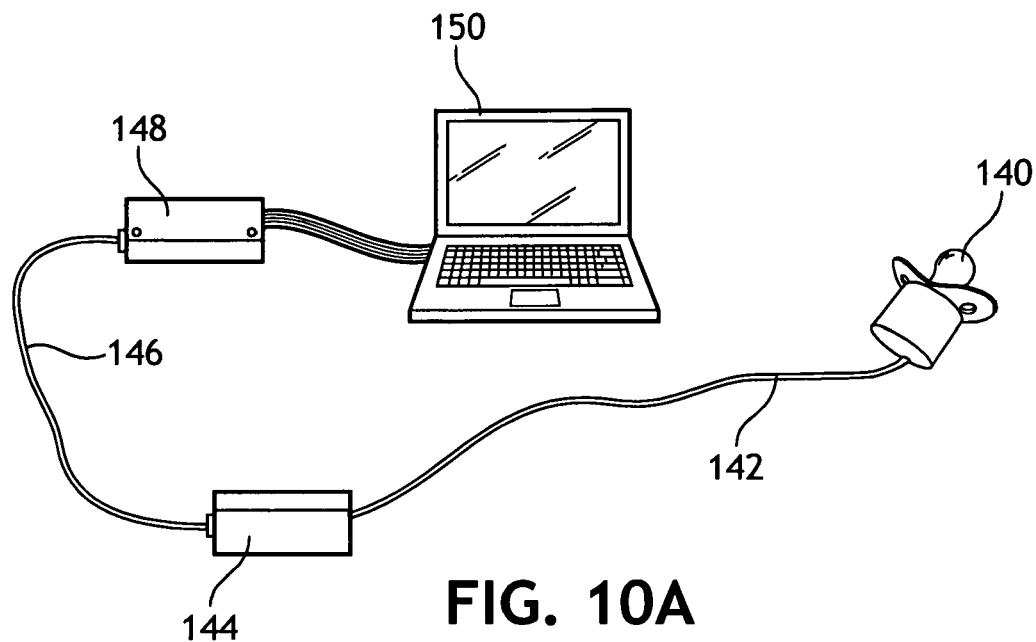

First, a device for detecting non-nutritive sucking events and/or rhythmic sucking patterns was made in accordance with the description in Example 2 above. This device 140 was then connected to other equipment as depicted in FIG. 10A. Four wires 142 exit the device (here, a modified pacifier). Two of these four wires were connected to a pair of ten-volt, direct-current batteries. The batteries were used to excite the transducer, and were positioned in a battery holder 144 available from Keystone Electronics Corp., a business having offices in Astoria, N.Y. The two remaining wires 146, which were associated with a 0 to 50 millivolt analog output from the pressure transducer, were connected to an analog-to-digital interface 148, in this case model number NI DAQCard-6036E (for PCMCIA; 200 kS/s, 16-bit, 16 Analog input multifunction DAQ), available from National Instruments Corp, a business having offices at North Mopac Expressway, Austin, Tex. It should be noted that other signal outputs, including analog signal outputs from pressure transducers, may be used, including, for example, AC voltage, DC voltage, AC current, or DC current. In addition, while not done here, the output signal may be amplified using appropriate electronic devices to boost the voltage or current to a higher value which is directly proportional to the pressure applied. Still another possible adaptation would be to utilize an apparatus commonly know as a voltage- or current-to-air pressure transducer (i.e. "I/P", or "V/P" transducer) to change a pressure transducer's analog voltage or current output signal to a mechanical signal such as a pneumatic air pressure output or a hydraulic pressure output in proportion to the analog signal input. For example, a 4-20 milliamp DC signal output from a pressure transducer can produce a proportional 3-15 PSI pneumatic signal output to enable or facilitate a mechanical motion (e.g., to perform a physical tack, or tasks).

The analog-to-digital interface does what its name states: it converts analog signals into a digital format that can be processed by, for example, a computer. The bit-rate conversion of the interface can be selected to provide adequate conversion of the signal from analog to digital. As noted with the selected interface identified above, we selected an interface with the capability of 16 bits per channel. The sampling frequency may be selected to accurately capture the frequency of the individual non-nutritive sucking events, and associated rhythmic sucking patterns, being produced. Generally, choosing a sampling frequency that is twice that of the frequency of the event (Nyquist criterion) will present a lower range for sampling frequency. Other sampling frequencies include 100 times the Nyquist criterion or 1000 times the Nyquist criterion. For our experiments, discussed in Example 5 below, we utilized a sampling frequency of 1000 Hertz. Additionally, to reduce our requirements for handling large amounts of data (e.g., when displaying the data visually), we at times filtered, i.e., reduced, the data to a frequency of 4 Hertz.

Here the analog-to-digital interface was connected to a Compaq EVO NG10C computer (designated by the number 150 in FIG. 10A). LabView software, version 6.1, was obtained from National Instruments. LabView software configures a computer to acquire, store, process, and display data transmitted to the computer from various sources, in this case digital values transmitted from the analog-to-digital converter. In this case, the software was used to process digital information corresponding to the analog signals, in millivolts, effected by an infant sucking on a modified pacifier equipped to detect non-nutritive sucking events.

Figure 10B:
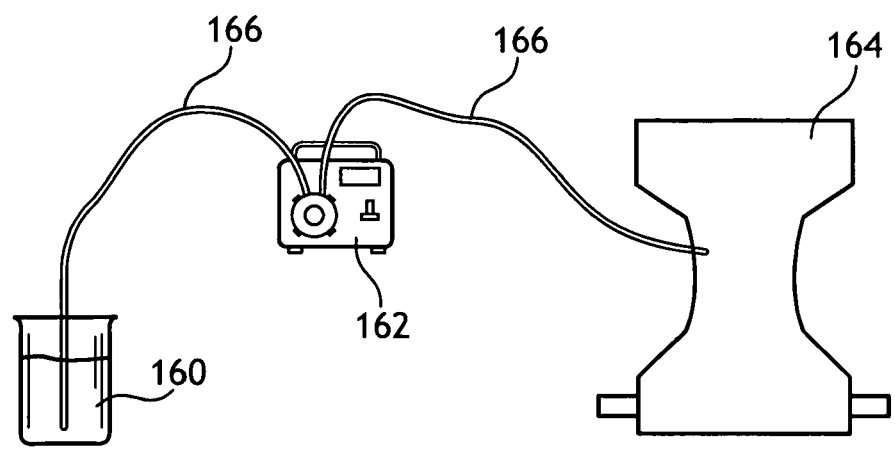

In addition to the sensor and information device used to detect and monitor the non-nutritive sucking events and/or rhythmic sucking patterns effected by an infant, the other components of the exemplary system are depicted in FIG. 10B, and included a liquid reservoir 160, in this case a glass beaker; a Masterflex peristaltic pump 162 available from Cole-Parmer Instrument Company (discussed above) for transporting liquid from the liquid reservoir to a disposable absorbent article 164; and flexible tubing 166 connecting the liquid reservoir to the point of insult in the disposable absorbent article.

Example 5

Test Showing Change in Rhythmic Sucking Pattern in Response to Liquid Insult to Disposable Article Worn by Infant A nurse fitted a 3- to 6-month-old female infant with a diaper 164 to which tubing was attached for purposes of introducing a liquid insult. The end of the tubing was positioned between the inner surface of the diaper and the infant's skin at a location proximate to the infant's genitalia (i.e., where the infant would typically insult a diaper with urine). The infant was placed in a prone position. The mother of the infant was present, and seen by the infant, during the test. The device 140 (in this case, a pacifier modified to comprise a pressure transducer) was placed in the infant's mouth by the mother or nurse. As expected, the infant sucked on the pacifier, with each of these non-nutritive sucking events being detected by a sensor (in this case a pressure transducer). The analog output of the transducer was converted by the analog-to-digital interface 148 into digital format for processing and display by the computer 150 configured with the LabView (version 6.1) software.

First non-nutritive sucking events effected by the infant were monitored to obtain a baseline for future comparisons (i.e., comparisons between the pattern of non-nutritive sucking events obtained in the absence of a controlled external stimulus and the pattern of non-nutritive sucking events obtained in the presence of a controlled external stimulus). As stated above, the mother of the infant was visible to the infant at all times. After approximately one or two minutes, a baseline value of 4.34 mV for the average amplitude of the non-nutritive sucking events (i.e., the rhythmic sucking pattern, or "RSP") was obtained. I.e., after one or two minutes the pattern of individual non-nutritive sucking events was stable and regular, and had the appearance of a repeating sawtooth pattern (with each tooth, or spike, corresponding to an increase in amplitude in mV due to the infant sucking on the pacifier). As discussed earlier, each suck flexes the nipple of the pacifier, causing a pressure change inside the nipple. The sensor selected for this exemplary system, a pressure transducer, detects these pressure changes in the form of a change in an analog output (in units of millivolts).

The Masterflex peristaltic pump 132 was then activated to prime the pump, which took approximately 5-10 seconds. "Priming" means the pump was turned on to remove any unwanted air pockets (in this case from the tubing). Liquid was not transported to the diaper worn by the infant while the pump was being primed. During this time, the average amplitude of the rhythmic sucking pattern increased to 6.75 mV. Apparently the sound of the activated pump, being sensed by the infant, translated into a response such that the amplitudes of some of the individual sucking events increased, resulting in an increase of the average amplitude for the collection of individual sucking events (i.e., the rhythmic sucking pattern). Shortly thereafter (e.g., 5-10 seconds after the pump was activated), the average amplitude of the individual non-nutritive sucking events returned to a value proximate to the baseline value of 4.34 mV.

After the pump was primed, the diaper was treated with two, 60 mL liquid insults, delivered at a volumetric flow rate of 300 mL per minute, with each of the two liquid insults separated by a 45 second pause. I.e., a first insult of 60 mL of liquid was delivered to the diaper at a volumetric flow rate of 300 mL per minute, followed by a 45 second pause. Then a second insult of 60 mL of liquid was delivered to the diaper at a volumetric flow rate of 300 mL per minute, followed by a 45 second pause. We had planned to apply a third and final insult of 60 mL of liquid (delivered to the diaper at a volumetric flow rate of 300 mL per minute), but the infant spit out the pacifier. The liquid that was delivered to the diaper was a 0.9% by weight NaCl solution, warmed to a temperature of 98.6° F.

The average amplitude of the rhythmic sucking pattern during the first insult was 4.79 mV. The average of 4.79 mV was calculated by taking the average of individual amplitudes of individual non-nutritive sucking events detected over the course of the liquid insult as well as the 45-second interval that followed. I.e., data was taken for a total of 57 seconds (12 seconds to deliver 60 mL at a volumetric flowrate of 300 mL per minute plus 45 seconds). The average amplitude of the rhythmic sucking pattern during this second insult was 5.25 mV (again, the average amplitude corresponds to the average of individual amplitudes taken over a 57-second interval—i.e., the 12 seconds taken to deliver 60 mL at a volumetric flowrate of 300 mL per minute plus 45 seconds).

The pump was then turned off, and the infant was fitted with a new diaper. After about five minutes, the same sequence of actions described above was followed again. The average amplitude for the baseline RSP was determined to be 4.2 mV. The average amplitude of the RSP during pump priming (apparently attributable to the infant detecting a change in the audible environment) increased to 5.8 mV. The average amplitudes during the first and second insults were 4.6 and 5.19 mV, respectively.

The data collected during these tests are summarized in Table 1 below. The data demonstrate that sensing non-nutritive sucking events and/or rhythmic sucking patterns may be used to provide indicia of an infant's perception of his or her environment, including the performance of, or changes to, a disposable absorbent article worn by the infant.

TABLE 1

Changes to Rhythmic Sucking Pattern

| | Average Amplitude (mV) | Frequency (Hz) | Standard Deviation of Average Amplitude (mv) | % Change Between Average Amplitude of Initial RSP and Average Amplitude of RSP Determined During Insult |
|---|---|---|---|---|
| First Experiment | | | | |
| Initial RSP | 4.34 | 1.38 | 1.57 | Not applicable |
| RSP During Priming of Pump | 6.75 | 1.53 | 2.45 | Not applicable |
| RSP During First Insult | 4.79 | 1.31 | 2.16 | 10 |
| RSP During Second Insult | 5.25 | 1.41 | 1.84 | 21 |
| Second Experiment | | | | |
| Initial RSP | 4.2 | 1.51 | 1.09 | Not applicable |
| RSP During Priming of Pump | 5.8 | 2.22 | 1.6 | Not applicable |
| RSP During First Insult | 4.62 | 1.59 | 1.16 | 10 |
| RSP During Second Insult | 5.19 | 1.35 | 1.71 | 24 |

Prophetic Example 6

Use of System for Evaluating a Disposable Article to Help Substantiate an Advertising Claim or Message A system, like the exemplary system discussed in Examples 4 and 5 above, is used to evaluate a number of infants wearing a selected disposable article to determine both an average amplitude for a baseline RSP and average amplitudes for RSPs corresponding to the addition of a selected quantity (or quantities) of a urine- or BM-simulant (or other such fluid or liquid). The test is repeated for a second selected disposable article so that the RSP average-amplitude values of the two tested articles can be compared. If the differences between the two tested articles are deemed different using an appropriate statistical or other basis, and this difference is attributable, in whole or in part, to the construction or performance of the tested articles, then the resulting data may be used to help substantiate a possible advertising claim or message regarding the performance of the articles as perceived by the tested infants. For example, if one tested article absorbed liquid more quickly than the second tested article, and the average-amplitude value during a liquid insult to the more absorbent article was significantly less than the average-amplitude value during a liquid insult to the less absorbent article, then this data might be used to support an advertising claim based on this difference.

Other approaches may be used for the above purpose. For example, rather than evaluate the average amplitude of a selected collection of individual non-nutritive sucking events, the frequency of said events might be evaluated. Alternatively, specific patterns of such events might be used to compare the performance of tested articles.

Prophetic Example 7

Use of System for Evaluating a Disposable Article to Change or Initiate a Research-and-Development Project or Program A system, like the exemplary system discussed in Examples 4 and 5 above, is used to evaluate a number of infants wearing a selected disposable article to determine both an average amplitude for a baseline RSP and average amplitudes for RSPs corresponding to the addition of a selected quantity (or quantities) of a urine- or BM-simulant (or other such fluid or liquid). The test is repeated for a second selected disposable article having a different feature, performance attribute, or material so that the RSP average-amplitude values of the two tested articles can be compared. If the differences between the two tested articles are deemed different using an appropriate statistical or other basis, and this difference is attributable, in whole or in part, to the difference in features, performance attributes, or materials between the two articles, then the resulting data may be used to initiate new research programs or projects, or change existing research programs or projects, based on average-amplitude data. For example, if one tested article absorbed liquid more quickly than the second tested article, such that the average-amplitude value during a liquid insult to the more absorbent article was significantly less than the average-amplitude value during a liquid insult to the less absorbent article, then this data might be used to support a decision to change, start, or terminate research projects or programs implicating one or more features, performance attributes, or materials of the tested articles.

Other approaches may be used for the above purpose. For example, rather than evaluate the average amplitude of a selected collection of individual non-nutritive sucking events, the frequency of said events might be evaluated. Alternatively, specific patterns of such events might be used to compare the performance of tested articles.

Prophetic Example 8

Use of a Modified Pacifier to Provide Indicia to a Caregiver Regarding the Health or Well Being of an Infant A pacifier similar to those identified in Examples 1, 2, and 3 above is further modified to include a visual display. Using color, images, numbers, symbols, letters, or the like, the pacifier effects a given display corresponding to one or more attributes of the individual, non-nutritive sucking events and/or rhythmic sucking patterns produced by the infant.

Prophetic Example 9

Use of System for Evaluating a Disposable Article to Identify Ranges of Values Corresponding to RSPs Indicative of States of Well Being of Infants A system, like the exemplary system discussed in Examples 4 and 5 above, is used to evaluate a number of infants wearing a selected disposable article to determine both an average amplitude for a baseline RSP and average amplitudes for RSPs corresponding to the addition of a selected quantity (or quantities) of a urine- or BM-simulant (or other such fluid or liquid). A sufficient number of infants are tested such that ranges of amplitudes, frequencies, or other characteristics of RSPs are identified that correspond to specific states of well being or stress. For example, if a selected population of infants wearing disposable articles that leak onto skin typically result in average amplitudes of RSPs in the range of 5-7 mV, and there is a statistical or other basis indicating that this range typically corresponds to infants' perceptions of such articles that leak, then a range will have been established that is indicative of an infant's perception of a given kind of performance of a disposable article.

We claim:

1. A system for evaluating a disposable article, the system comprising:
    a first sensor adapted to detect non-nutritive sucking events produced by an infant;
    a second sensor adapted to detect fluid flowing to, or present in, a disposable article worn by the infant; and
    an information device operatively connected to the first sensor, said information device adapted to accomplish one or more of receiving, storing, processing, displaying, or transmitting information corresponding to a change in the non-nutritive sucking events detected by the first sensor in response to the second sensor detection.

2. The system of claim 1 wherein the first sensor is a pressure transducer adapted to detect the non-nutritive sucking events.

3. The system of claim 2 wherein the pressure transducer is attached to a pacifier.

4. The system of claim 1 wherein the information device comprises a storage device.

5. The system of claim 1 wherein the storage device is RAM, ROM, PROM, EPROM, or RFID.

6. The system of claim 5 wherein the information device is attached to a pacifier.

7. The system of claim 1 wherein the information device is a computer.

8. The system of claim 1 wherein the second sensor is adapted to detect temperature; humidity; current; mass flow rate; volumetric flow rate; mass; volume; opacity; transmittance; wavelength; the presence and/or concentration of dissolved solids, chemical compounds, ionic compounds, proteins, bacteria, microorganisms, suspended solids, or precipitates; or some combination of these.

9. A message adapted to be communicated to consumers, wherein the message comprises information produced using the system of claim 1.

10. The system of claim 1 wherein a second information device is operatively connected to the second sensor, said second information device adapted to accomplish one or more of receiving, storing, processing, displaying, or transmitting information corresponding to the second sensor's detection of fluid flowing to, or present in, the disposable article.

11. The system of claim 1 wherein the information device is operatively connected to the first sensor by conductive wire, a pneumatic connection, a hydraulic connection, a connection using a portion of the electromagnetic spectrum, or some combination of these.

12. A pacifier adapted to detect non-nutritive sucking events, the pacifier comprising:
    a nipple;
    a base attached to said nipple;
    a sensor attached to said base, said sensor adapted to detect non-nutritive sucking events produced by an infant sucking on the nipple; and
    an information device attached to said base and operatively connected to the sensor, said information device adapted to accomplish one or more of receiving, storing, processing, displaying, or transmitting information corresponding to the non-nutritive sucking events detected by the sensor; said information comprises a psychological state of the infant as indicated by the non-nutritive sucking event detected by the sensor;
    wherein the information device comprises a display adapted to present a graphical image corresponding to said psychological state.

13. The pacifier of claim 12 wherein the sensor is a pressure transducer adapted to detect non-nutritive sucking events.

14. The pacifier of claim 12 wherein the information device comprises a storage device.

15. The pacifier of claim 14 wherein the storage device is RAM, ROM, PROM, EPROM, or RFID.

16. A message adapted to be communicated to consumers, wherein the message comprises information produced using the device of claim 12.

17. A method for evaluating the performance of a first disposable article, the method comprising:
    (a) detecting non-nutritive sucking events produced by an infant wearer of the first disposable article;
    (b) detecting fluid flowing to, or present in, the first disposable article worn by the infant; and
    (c) relating the detected non-nutritive sucking events to the detected flow of fluid to, or presence of fluid in, the first disposable article.

18. The method of claim 17 further comprising:
    repeating steps 17(a), 17(b), and 17(c) for a second disposable article; and
    comparing the relationship obtained for the first disposable article to the relationship obtained for the second disposable article, or
    comparing the detected non-nutritive sucking events produced by an infant wearer of the first disposable article to the detected non-nutritive sucking events produced by an infant wearer of the second disposable article, or
    comparing the detected fluid flowing to, or present in, the first disposable article worn by the infant to the detected fluid flowing to, or present in, the second disposable article worn by the infant, or
    some combination of these.

19. The method of claim 17 further comprising communicating a message based on said relationship to consumers.

20. The method of claim 18 further comprising communicating a message based on said comparison to consumers.

21. A research-and-development method directed to changing the functional performance, product specifications, or materials of construction of a disposable article, wherein said research-and-development effort comprising the steps of evaluating non-nutritive sucking events and correlating said events with the functional performance, product specifications, or materials of construction of the disposable article.

22. A system for evaluating a disposable article, the system comprising:
   a first sensor adapted to detect non-nutritive sucking events produced by an infant;
   a second sensor adapted to detect a property of one or more components of the disposable article worn by the infant; and
   an information device operatively connected to the first sensor and the second sensor, said information device adapted to accomplish one or more of receiving, storing, processing, displaying, or transmitting information corresponding to the non-nutritive sucking events detected by the first sensor in response to a property of one or more components of the disposable article worn by the infant as detected by the second sensor.

23. A method for evaluating the performance of a disposable article, the method comprising:
   (a) detecting non-nutritive sucking events produced by an infant wearer of the disposable article;
   (b) characterizing a change the disposable to a disposable article worn by the infant; and
   (c) relating the detected non-nutritive sucking events to the characterized change to the disposable article.

\* \* \* \* \*